US009840718B2

(12) United States Patent
Solodushko et al.

(10) Patent No.: US 9,840,718 B2
(45) Date of Patent: Dec. 12, 2017

(54) MINIMAL *PIGGYBAC* VECTORS FOR GENOME INTEGRATION

(71) Applicant: University of South Alabama, Mobile, AL (US)

(72) Inventors: Victor Solodushko, Mobile, AL (US); Brian Fouty, Spanish Fort, AL (US); Vira Bitko, Mobile, AL (US)

(73) Assignee: University of South Alabama, Mobile, AL (US)

( * ) Notice: Subject to any disclaimer, the term of this patent is extended or adjusted under 35 U.S.C. 154(b) by 0 days.

(21) Appl. No.: 14/904,625

(22) PCT Filed: Jul. 11, 2014

(86) PCT No.: PCT/US2014/046366
§ 371 (c)(1),
(2) Date: Jan. 12, 2016

(87) PCT Pub. No.: WO2015/006700
PCT Pub. Date: Jan. 15, 2015

(65) Prior Publication Data
US 2016/0160235 A1  Jun. 9, 2016

Related U.S. Application Data

(60) Provisional application No. 61/845,652, filed on Jul. 12, 2013.

(51) Int. Cl.
C12N 15/86    (2006.01)
C12N 15/11    (2006.01)
C12N 15/12    (2006.01)
C12N 15/85    (2006.01)
C12N 9/12     (2006.01)

(52) U.S. Cl.
CPC ........... *C12N 15/85* (2013.01); *C12N 9/1241* (2013.01); *C12Y 207/07* (2013.01)

(58) Field of Classification Search
None
See application file for complete search history.

(56) References Cited

U.S. PATENT DOCUMENTS

| | | |
|---|---|---|
| 5,500,365 A | 3/1996 | Fischhoff et al. |
| 6,551,825 B1 | 4/2003 | Shirk et al. |
| 6,773,914 B1 | 8/2004 | Handler |
| 6,962,810 B2 | 11/2005 | Fraser et al. |
| 7,005,296 B1 | 2/2006 | Handler |
| 7,064,246 B2 | 6/2006 | MacRae |
| 7,105,343 B1 | 9/2006 | Fraser et al. |
| 7,129,083 B1 | 10/2006 | Handler |
| 7,932,088 B1 | 4/2011 | Adams et al. |
| 8,124,404 B2 | 2/2012 | Alphey |
| 2002/0173634 A1 | 11/2002 | Fraser et al. |
| 2006/0210977 A1 | 9/2006 | Kaminski |
| 2007/0204356 A1 | 8/2007 | Fraser |
| 2009/0042297 A1 | 2/2009 | George, Jr. et al. |
| 2010/0154070 A1 | 6/2010 | Xu et al. |
| 2010/0178696 A1* | 7/2010 | Wu .................... C12N 15/1051 435/320.1 |
| 2010/0221824 A1 | 9/2010 | Fraser |
| 2010/0240133 A1 | 9/2010 | Brivanlou et al. |
| 2011/0047635 A1 | 2/2011 | Moisyadi et al. |
| 2011/0311506 A1 | 12/2011 | Craig |

FOREIGN PATENT DOCUMENTS

| | | |
|---|---|---|
| WO | 2005003364 A2 | 1/2005 |
| WO | 2006122442 A1 | 11/2006 |

OTHER PUBLICATIONS

Zhao et al, PiggyBac transposon vectors: the tools of the human gene encoding, Transl Lung Cancer Res 2016;5(1):120-125.*
Zhuang et al, The relationship between internal domain sequences of piggyBac and its transposition efficiency in BmN cells and Bombyx mori, Acta Biochim Biophys Sin 2010, 42: 426-431.*
Trichoplusia ni transposon PiggyBac-Hi5 transposase gene, complete cds GenBank: DQ340395.1 FASTA Graphics, downloaded Feb. 7, 2017.*
Cadiñanos et al. "Generation of an Inducible and Optimized piggyBac Transposon System." Nucleic Acids Res. 35(2007):e87.
Cary et al. "Transposon Mutagenesis of Baculoviruses: Analysis of Trichoplusia ni Transposon IFP2 Inserttions Within the FP-Locus of Nuclear Polyhedrosis Viruses." Virol. 172(989):156-169.
Elick et al. "Analysis of the cis-Acting DNA Elements Required for piggyBac Transpoable Element Excision." Mol. Gen. Genet. 255(1997):605-610.
Elick et al. "Excision of the piggyBac Transposable Element in vitro is a Precise Event that is Enhanced by the Expression of its Encoded Transposase." Genetica. 98(1996):33-41.
Fraser et al. "Precise Excision of TTAA-Specific Lipdopteran Transposons piggyBac (IFP2) and tagalong (TFP3) from the Baculovirus Genome in Cell Lines from Two Species of *Lipidoptera*." Insect Mol. Biol. 5(1996):141-151.
Handler et al. "The Lepidopteran Transposon Vector, piggyBac, Mediates Germ-Line Transformation in the Mediterreanean Fruit Fly." PNAS.95(1998):7520-7525.
Kahlig et al. "Multiplexed Transposon-Mediated Stable Gene Transfer in Human Cells." PNAS. 15(2007):1343-1348.
Kawakami et al. "Nonviral Approaches for Targeted Delivery of Plasmid DNA and Oligonucleotide." J. Pharm. Sci. 97(2008):726-745.
Kobayashi et al. "Gene Delivery to Embryonic Stem Cells." Birth Defects Res. C Embryo Today. 75.1(2005):10-18.
Lakshmipathy et al. "Gene Transfer via Nucleofection into Adult and Embryonic Stem Cells." Methods Mol. Biol. 407(2007):115-126.
Li et al. "PiggyBac Internal Sequences are Necessary for Efficient Transformation of Target Genomes." Insect Mol. Biol. 14.1(2005):17-30.

(Continued)

*Primary Examiner* — Maria Marvich
(74) *Attorney, Agent, or Firm* — Burns & Levinson LLP; Shawn P. Foley

(57) ABSTRACT

Disclosed are genetic delivery systems that utilize genetic elements of the piggyBac family transposon system, and methods of introducing nucleic acid into target cells using the genetic delivery systems.

28 Claims, 7 Drawing Sheets

(56) References Cited

OTHER PUBLICATIONS

Li et al. "PiggyBac-Mediated Transposition in *Drosophila melanogaster*: An Evaluation of the Use of Constitutive Promoters to Control Transposase Gene Expression." Insect Mol. Biol. 10(2001):447-455.
Li et al. "The Minimum Internal and External Sequence Requirements for Transposition of the Eukaryotic Transformation Vector piggyBac." Mol. Genet. Genomics. 266(2001):190-198.
Li et al. "Non-Viral is Superior to Viral Gene Delivery." J. Control. Release. 123.3(2007):181-183.
Li et al. "Mobilization of Giant piggyBac Transposons in the Mouse Genome." Nucleic Acids Res. 39(2011):e148.
Meir et al. "Genome-Wide Target Profiling of piggyBac and Tol2 in HEK 293: Pros and Cons for Gene Discovery and Gene Therapy." BMC Biotechnol. 11(2011):28.
Meir et al. "Transposon-Based Vector Systems for Gene Therapy Clinical Trials: Challenges and Considerations." Chang. Gung. Med. J. 34.6(2011):565-579.
Mossine et al. "PiggyBac Transposon Plus Insulators Overcome Epigenetic Silencing to Provide for Stable Signaling Pathway Reporter Cell Lines." PLoS One. 8.12(2013):e85494.
Nakanishi et al. "PiggyBac Transposon-Mediated Long-Term Gene Expression in Mice." Mol. Ther. 18.4(2010):707-714.
Niwa et al. "Efficient Selection for High-Expression Transfectants with a Novel Eukaryotic Vector." Gene. 108.2(1991)193-199.
Rostovskaya et al. "Transposon-Mediated BAC Transgenesis in Human ES Cells." Nucleic Acids Res. 40.19(2012):e150.
Saha et al. "Evaluating the Potential for Undesired Genomic Effects of the piggyBac Tranposon System in Human Cells." Nucleic Acids Res. 43.3(2015):1770-1782.

Shi et al. "Construction and Characterization of New piggyBac Vectors for Constitutive or Inducible Expression of Heterologous Gene Pairs and the Identification of a Previously Unrecognized Activator Sequence in piggyBac." BMC Biotechnol. 7(2007):5.
Solodushko et al. "Minimal piggyBac Vectors for Chromatin Integration." Gene Therapy. 21(2014):1-9.
Troyanovsky et al. "Simple Viral/Minimal piggyBac Hybrid Vectors for Stable Production of Self-Inactivating Gamma-Retroviruses." BMC Res. Notes. 8(2015):379.
Urasaki et al. "Functional Dissection of the Tol2 Transposable Element Identified the Minimal I-Sequence and a Highly Repetitive Sequence in the Subterminal Region Essential for Transposition." Genetics. 174(2006):639-649.
Wang et al. "Chromosomal Transposition of piggyBac in Mouse Embryonic Stems Cells." PNAS. 105(2008)9290-9295.
Wilson et al. "PiggyBac Transposon-mediated Gene Transfer in Human Cells." Mol. Ther. 15.1(2007):139-145.
Wu et al. "PiggyBac is a Flexible and Highly Active Transposon as Compared to Sleeping Beauty, Tol2, and Mos1 in Mammalian Cells." PNAS. 103.41(2006):15008-15013.
Yusa et al. "Generation of Transgene-Free Induced Pluripotent Mouse Stem Cells by the piggyBac Transposon." Nat. Methods. 6.5(2009):363-369.
Zhang et al. "The Relationship Between Internal Domain Sequences of piggyBac and its Transposition Efficiency in BmN Cells and Bombyx mori." Acta Biochim. Biophys. Sin. 42.6(2010):426-431.
Zayed et al. "Development of Hyperactive Sleeping Beauty Transposon Vectors by Mutational Analysis." Mol. Ther. 9.2 (2004):292-304.

* cited by examiner

SEQUENCE LISTING

<160> NUMBER OF SEQ ID NOS: 22

<210> SEQ ID NO 1
<211> LENGTH: 2472
<212> TYPE: DNA
<213> ORGANISM: Trichoplusia ni

<400> SEQUENCE: 1

| | | | | | | |
|---|---|---|---|---|---|---|
| ccctagaaag | atagtctgcg | taaaattgac | gcatgcattc | ttgaaatatt | gctctctctt | 60 |
| tctaaatagc | gcgaatccgt | cgctgtgcat | ttaggacatc | tcagtcgccg | cttggagctc | 120 |
| ccgtgaggcg | tgcttgtcaa | tgcggtaagt | gtcactgatt | ttgaactata | acgaccgcgt | 180 |
| gagtcaaaat | gacgcatgat | tatcttttac | gtgactttta | agatttaact | catacgataa | 240 |
| ttatattgtt | atttcatgtt | ctacttacgt | gataacttat | tatatatata | ttttcttgtt | 300 |
| atagatatcg | tgactaatat | ataataaaat | gggtagttct | ttagacgatg | agcatatcct | 360 |
| ctctgctctt | ctgcaaagcg | atgacgagct | tgttggtgag | gattctgaca | gtgaaatatc | 420 |
| agatcacgta | agtgaagatg | acgtccagag | cgatacagaa | gaagcgttta | tagatgaggt | 480 |
| acatgaagtg | cagccaacgt | caagcggtag | tgaaatatta | gacgaacaaa | atgttattga | 540 |
| acaaccaggt | tcttcattgg | cttctaacag | aatcttgacc | ttgccacaga | ggactattag | 600 |
| aggtaagaat | aaacattgtt | ggtcaacttc | aaagtccacg | aggcgtagcc | gagtctctgc | 660 |
| actgaacatt | gtcagatctc | aaagaggtcc | gacgcgtatg | tgccgcaata | tatatgaccc | 720 |
| acttttatgc | ttcaaactat | tttttactga | tgagataatt | tcggaaattg | taaaatggac | 780 |
| aaatgctgag | atatcattga | aacgtcggga | atctatgaca | ggtgctacat | tcgtgacac | 840 |
| gaatgaagat | gaaatctatg | ctttctttgg | tattctggta | atgacagcag | tgagaaaaga | 900 |
| taaccacatg | tccacagatg | acctctttga | tcgatctttg | tcaatggtgt | acgtctctgt | 960 |
| aatgagtcgt | gatcgttttg | attttttgat | acgatgtctt | agaatggatg | acaaaagtat | 1020 |
| acggcccaca | cttcgagaaa | acgatgtatt | tactcctgtt | agaaaaatat | gggatctctt | 1080 |
| tatccatcag | tgcatacaaa | attacactcc | aggggctcat | ttgaccatag | atgaacagtt | 1140 |
| acttggtttt | agaggacggt | gtccgtttag | gatgtatatc | ccaaacaagc | caagtaagta | 1200 |
| tggaataaaa | atcctcatga | tgtgtgacag | tggtacgaag | tatatgataa | atggaatgcc | 1260 |
| ttatttggga | agaggaacac | agaccaacgg | agtaccactc | ggtgaatact | acgtgaagga | 1320 |
| gttatcaaag | cctgtgcacg | tgtagttgtcg | taatattacg | tgtgacaatt | ggttcacctc | 1380 |
| aatcccttg | gcaaaaaact | tactacaaga | accgtataag | ttaaccattg | tgggaaccgt | 1440 |
| gcgatcaaac | aaacgcgaga | taccggaagt | actgaaaaac | agtcgctcca | ggccagtggg | 1500 |
| aacatcgatg | ttttgttttg | acggacccct | tactctcgtc | tcatataaac | cgaagccagc | 1560 |
| taagatggta | tacttattat | catcttgtga | tgaggatgct | tctatcaacg | aaagtaccgg | 1620 |
| taaaccgcaa | atggttatgt | attataatca | aactaaaggc | ggagtggaca | cgctagacca | 1680 |
| aatgtgttct | gtgatgacct | gcagtaggaa | gacgaatagg | tggcctatgg | cattattgta | 1740 |
| cggaatgata | aacattgcct | gcataaattc | ttttattata | tacagccata | atgtcagtag | 1800 |
| caagggagaa | aaggttcaaa | gtcgcaaaaa | atttatgaga | aacctttaca | tgagcctgac | 1860 |
| gtcatcgttt | atgcgtaagc | gtttagaagc | tcctactttg | aagagatatt | tgcgcgtaaa | 1920 |
| tatctctaat | attttgccaa | atgaagtgcc | tggtacatca | gatgacagta | ctgaagagcc | 1980 |
| agtaatgaaa | aaacgtactt | actgtactta | ctgcccctct | aaaataaggc | gaaaggcaaa | 2040 |
| tgcatcgtgc | aaaaaatgca | aaaaagttat | ttgtcgagag | cataatattg | atatgtgcca | 2100 |

```
aagttgtttc tgactgacta ataagtataa tttgtttcta ttatgtataa gttaagctaa    2160
ttacttattt tataatacaa catgactgtt tttaaagtac aaaataagtt tatttttgta    2220
aaagagagaa tgtttaaaag ttttgttact ttatagaaga aattttgagt ttttgttttt    2280
ttttaataaa taaataaaca taaataaatt gtttgttgaa tttattatta gtatgtaagt    2340
gtaaatataa taaaacttaa tatctattca aattaataaa taaacctcga tatacagacc    2400
gataaaacac atgcgtcaat tttacgcatg attatcttta acgtacgtca caatatgatt    2460
atctttctag gg                                                       2472

<210> SEQ ID NO 2
<211> LENGTH: 35
<212> TYPE: DNA
<213> ORGANISM: Trichoplusia ni

<400> SEQUENCE: 2
ccctagaaag atagtctgcg taaaattgac gcatg                                35

<210> SEQ ID NO 3
<211> LENGTH: 644
<212> TYPE: DNA
<213> ORGANISM: Trichoplusia ni

<400> SEQUENCE: 3
cattcttgaa atattgctct ctctttctaa atagcgcgaa tccgtcgctg tgcatttagg     60
acatctcagt cgccgcttgg agctcccgtg aggcgtgctt gtcaatgcgg taagtgtcac    120
tgattttgaa ctataacgac cgcgtgagtc aaaatgacgc atgattatct tttacgtgac    180
ttttaagatt taactcatac gataattata ttgttatttc atgttctact tacgtgataa    240
cttattatat atatattttc ttgttataga tatcgtgact aatatataat aaaatgggta    300
gttctttaga cgatgagcat atcctctctg ctcttctgca aagcgatgac gagcttgttg    360
gtgaggattc tgacagtgaa atatcagatc acgtaagtga agatgacgtc cagagcgata    420
cagaagaagc gtttatagat gaggtacatg aagtgcagcc aacgtcaagc ggtagtgaaa    480
tattagacga acaaaatgtt attgaacaac caggttcttc attggcttct aacagaatct    540
tgaccttgcc acagaggact attagaggta agaataaaca ttgttggtca acttcaaagt    600
ccacgaggcg tagccgagtc tctgcactga acattgtcag atct                    644

<210> SEQ ID NO 4
<211> LENGTH: 1370
<212> TYPE: DNA
<213> ORGANISM: Trichoplusia ni

<400> SEQUENCE: 4
caaagaggtc cgacgcgtat gtgccgcaat atatgacc cactttatg cttcaaacta        60 ttttttactg atgagataat ttcggaaatt gtaaaatgga caaatgctga gatatcattg    120
aaacgtcggg aatctatgac aggtgctaca tttcgtgaca cgaatgaaga tgaaatctat    180
gctttctttg gtattctggt aatgacagca gtgagaaaag ataaccacat gtccacagat    240
gacctctttg atcgatcttt gtcaatggtg tacgtctctg taatgagtcg tgatcgtttt    300
gattttttga tacgatgtct tagaatggat gacaaaagta tacggcccac acttcgagaa    360
aacgatgtat ttactcctgt tagaaaaata tgggatctct ttatccatca gtgcatacaa    420
aattacactc caggggctca tttgaccata gatgatgggt agttctttag acgatgagca    480
```

-continued

```
tatcctctct gctcttctgc aaagcgatga cgagcttgtt ggtgaggatt ctgacagtga    540
aatatcagat cacgtaagtg aagatgacgt ccagagcgat acagaagaag cgtttataga    600
tgaggtacat gaagtgcagc caacgtcaag cggtagtgaa atattagacg aacaaaatgt    660
tattgaacaa ccaggttctt cattggcttc taacagaatc ttgaccttgc cacagaggac    720
tattagaggt aagaataaac attgttggtc aacttcaaag tccacgaggc gtagccgagt    780
ctctgcactg aacattgtca gatctaacag ttacttggtt ttagaggacg gtgtccgttt    840
aggatgtata tcccaaacaa gccaagtaag tatggaataa aaatcctcat gatgtgtgac    900
agtggtacga agtatatgat aaatggaatg ccttatttgg gaagaggaac acagaccaac    960
ggagtaccac tcggtgaata ctacgtgaag gagttatcaa agcctgtgca cggtagttgt   1020
cgtaatatta cgtgtgacaa ttggttcacc tcaatccctt tggcaaaaaa cttactacaa   1080
gaaccgtata agttaaccat tgtgggaacc gtgcgatcaa acaaacgcga gataccggaa   1140
gtactgaaaa acagtcgctc caggccagtg ggaacatcga tgttttgttt tgacggaccc   1200
cttactctcg tctcatataa accgaagcca gctaagatgg tatacttatt atcatcttgt   1260
gatgaggatg cttctatcaa cgaaagtacc ggtaaaccgc aaatggttat gtattataat   1320
caaactaaag gcggagtgga cacgctagac caaatgtgtt ctgtgatgac              1370
```

<210> SEQ ID NO 5
<211> LENGTH: 711
<212> TYPE: DNA
<213> ORGANISM: Trichoplusia ni

<400> SEQUENCE: 5

```
ctgcagtagg aagacgaata ggtggcctat ggcattattg tacggaatga taaacattgc     60
ctgcataaat tcttttatta tatacagcca taatgtcagt agcaagggag aaaaggttca    120
aagtcgcaaa aaatttatga gaaaccttta catgagcctg acgtcatcgt ttatgcgtaa    180
gcgtttagaa gctcctactt tgaagagata tttgcgcgat aatatctcta atattttgcc    240
aaatgaagtg cctggtacat cagatgacag tactgaagag ccagtaatga aaaaacgtac    300
ttactgtact tactgcccct ctaaaataag gcgaaaggca aatgcatcgt gcaaaaaatg    360
caaaaaagtt atttgtcgag agcataatat tgatatgtgc caaagttgtt tctgactgac    420
taataagtat aatttgtttc tattatgtat aagttaagct aattacttat tttataatac    480
aacatgactg tttttaaagt acaaaataag tttatttttg taaaagagag aatgtttaaa    540
agttttgtta ctttatagaa gaaattttga gtttttgttt ttttttaata aataaataaa    600
cataaataaa ttgtttgttg aatttattat tagtatgtaa gtgtaaatat aataaaactt    660
aatatctatt caaattaata aataaacctc gatatacaga ccgataaaac a             711
```

<210> SEQ ID NO 6
<211> LENGTH: 2409
<212> TYPE: DNA
<213> ORGANISM: Trichoplusia ni

<400> SEQUENCE: 6

```
ccctagaaag atagtctgcg taaaattgac gcatgcattc ttgaaatatt gctctctctt     60
tctaaatagc gcgaatccgt cgctgtgcat ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatcttttac gtgactttta agatttaact catacgataa    240
ttatattgtt atttcatgtt ctacttacgt gataacttat tatatatata ttttcttgtt    300
```

```
atagatatcg tgactaatat ataataaaat gggtagttct ttagacgatg agcatatcct    360
ctctgctctt ctgcaaagcg atgacgagct tgttggtgag gattctgaca gtgaaatatc    420
agatcacgta agtgaagatg acgtccagag cgatacagaa gaagcgttta tagatgaggt    480
acatgaagtg cagccaacgt caagcggtag tgaaatatta gacgaacaaa atgttattga    540
acaaccaggt tcttcattgg cttctaacag aatcttgacc ttgccacaga ggactattag    600
aggtaagaat aaacattgtt ggtcaacttc aaagtccacg aggcgtagcc gagtctctgc    660
actgaacatt gtcagatctc aaagaggtcc gacgcgtatg tgccgcaata tatatgaccc    720
acttttatgc ttcaaactat tttttactga tgagataatt tcggaaattg taaaatggac    780
aaatgctgag atatcattga aacgtcggga atctatgaca ggtgctacat ttcgtgacac    840
gaatgaagat gaaatctatg ctttctttgg tattctggta atgacagcag tgagaaaaga    900
taaccacatg tccacagatg acctctttga tcgatctttg tcaatggtgt acgtctctgt    960
aatgagtcgt gatcgttttg attttttgat acgatgtctt agaatggatg acaaaagtat   1020
acggcccaca cttcgagaaa acgatgtatt tactcctgtt agaaaaatat gggatctctt   1080
tatccatcag tgcatacaaa attacactcc aggggctcat ttgaccatag atgaacagtt   1140
acttggtttt agaggacggt gtccgtttag gatgtatatc ccaaacaagc caagtaagta   1200
tggaataaaa atcctcatga tgtgtgacag tggtacgaag tatatgataa atggaatgcc   1260
ttatttggga agaggaacac agaccaacgg agtaccactc ggtgaatact acgtgaagga   1320
gttatcaaag cctgtgcacg gtagttgtcg taatattacg tgtgacaatt ggttcacctc   1380 aatcccttg gcaaaaaact tactacaaga accgtataag ttaaccattg tgggaaccgt   1440
gcgatcaaac aaacgcgaga taccggaagt actgaaaaac agtcgctcca ggccagtggg   1500
aacatcgatg ttttgttttg acggacccct tactctcgtc tcatataaac cgaagccagc   1560
taagatggta tacttattat catcttgtga tgaggatgct tctatcaacg aaagtaccgg   1620
taaaccgcaa atggttatgt attataatca aactaaaggc ggagtggaca cgctagacca   1680
aatgtgttct gtgatgacct gcagtaggaa gacgaatagg tggcctatgg cattattgta   1740
cggaatgata aacattgcct gcataaaattc ttttattata tacagccata atgtcagtag   1800
caagggagaa aaggttcaaa gtcgcaaaaa atttatgaga aacctttaca tgagcctgac   1860
gtcatcgttt atgcgtaagc gtttagaagc tcctactttg aagagatatt tgcgcgataa   1920
tatctctaat attttgccaa atgaagtgcc tggtacatca gatgacagta ctgaagagcc   1980
agtaatgaaa aaacgtactt actgtactta ctgcccctct aaaataaggc gaaaggcaaa   2040
tgcatcgtgc aaaaaatgca aaaaagttat ttgtcgagag cataatattg atatgtgcca   2100
aagttgtttc tgactgacta ataagtataa tttgtttcta ttatgtataa gttaagctaa   2160
ttacttattt tataatacaa catgactgtt tttaaagtac aaaataagtt tattttttgta   2220 aaagagagaa tgtttaaaag ttttgttact ttatagaaga aatttttgagt ttttgttttt   2280 ttttaataaa taaataaaca taaataaatt gtttgttgaa tttattatta gtatgtaagt   2340
gtaaatataa taaaacttaa tatctattca aattaataaa taaacctcga tatacagacc   2400
gataaaaca                                                            2409
```

<210> SEQ ID NO 7
<211> LENGTH: 63
<212> TYPE: DNA
<213> ORGANISM: Trichoplusia ni

<400> SEQUENCE: 7

```
catgcgtcaa ttttacgcat gattatcttt aacgtacgtc acaatatgat tatctttcta    60
ggg                                                                  63
```

<210> SEQ ID NO 8
<211> LENGTH: 679
<212> TYPE: DNA
<213> ORGANISM: Trichoplusia ni

<400> SEQUENCE: 8

```
ccctagaaag atagtctgcg taaaattgac gcatgcattc ttgaaatatt gctctctctt    60
tctaaatagc gcgaatccgt cgctgtgcat ttaggacatc tcagtcgccg cttggagctc   120
ccgtgaggcg tgcttgtcaa tgcggtaagt gtcactgatt tgaactata acgaccgcgt    180
gagtcaaaat gacgcatgat tatctttttac gtgactttta agatttaact catacgataa  240
ttatattgtt atttcatgtt ctacttacgt gataacttat tatatatata ttttcttgtt   300
atagatatcg tgactaatat ataataaaat gggtagttct ttagacgatg agcatatcct   360
ctctgctctt ctgcaaagcg atgacgagct tgttggtgag gattctgaca gtgaaatatc   420
agatcacgta agtgaagatg acgtccagag cgatacagaa gaagcgttta tagatgaggt  480
acatgaagtg cagccaacgt caagcggtag tgaaatatta gacgaacaaa atgttattga  540
acaaccaggt tcttcattgg cttctaacag aatcttgacc ttgccacaga ggactattag  600
aggtaagaat aaacattgtt ggtcaacttc aaagtccacg aggcgtagcc gagtctctgc  660
actgaacatt gtcagatct                                                679
```

<210> SEQ ID NO 9
<211> LENGTH: 2144
<212> TYPE: DNA
<213> ORGANISM: Trichoplusia ni

<400> SEQUENCE: 9

```
atgggtagtt cttagacga tgagcatatc ctctctgctc ttctgcaaag cgatgacgag    60
cttgttggtg aggattctga cagtgaaata tcagatcacg taagtgaaga tgacgtccag   120
agcgatacag aagaagcgtt tatagatgag gtacatgaag tgcagccaac gtcaagcggt   180
agtgaaatat tagacgaaca aaatgttatt gaacaaccag gttcttcatt ggcttctaac   240
agaatcttga ccttgccaca gaggactatt agaggtaaga ataaacattg ttggtcaact   300
tcaaagtcca cgaggcgtag ccgagtctct gcactgaaca ttgtcagatc tcaaagaggt   360
ccgacgcgta tgtgccgcaa tatatatgac ccactttat gcttcaaact attttttact    420
gatgagataa tttcggaaat tgtaaaatgg acaaatgctg agatatcatt gaaacgtcgg   480
gaatctatga caggtgctac atttcgtgac acgaatgaag atgaaatcta tgctttcttt   540
ggtattctgg taatgacagc agtgagaaaa gataaccaca tgtccacaga tgacctcttt   600
gatcgatctt tgtcaatggt gtacgtctct gtaatgagtc gtgatcgttt tgattttttg   660
atacgatgtc ttagaatgga tgacaaaagt atacggccca cacttcgaga aaacgatgta   720
tttactcctg ttagaaaaat atgggatctc tttatccatc agtgcataca aaattacact   780
ccaggggctc atttgaccat agatgaacag ttacttggtt ttagaggacg tgtccgtttc   840
aggatgtata tcccaaacaa gccaagtaag tatggaataa aaatcctcat gatgtgtgac   900
agtggtacga agtatatgat aaatggaatg ccttatttgg gaagaggaac acagaccaac   960
ggagtaccac tcggtgaata ctacgtgaag gagttatcaa agcctgtgca cggtagttgt  1020
```

```
cgtaatatta cgtgtgacaa ttggttcacc tcaatccctt tggcaaaaaa cttactacaa    1080
gaaccgtata agttaaccat tgtgggaacc gtgcgatcaa acaaacgcga gataccggaa    1140
gtactgaaaa acagtcgctc caggccagtg ggaacatcga tgttttgttt tgacggaccc    1200
cttactctcg tctcatataa accgaagcca gctaagatgg tatacttatt atcatcttgt    1260
gatgaggatg cttctatcaa cgaaagtacc ggtaaaccgc aaatggttat gtattataat    1320
caaactaaag gcggagtgga cacgctagac caaatgtgtt ctgtgatgac ctgcagtagg    1380
aagacgaata ggtggcctat ggcattattg tacggaatga taaacattgc ctgcataaat    1440
tcttttatta tatacagcca taatgtcagt agcaagggag aaaaggttca aagtcgcaaa    1500
aaatttatga gaaaccttta catgagcctg acgtcatcgt ttatgcgtaa gcgtttagaa    1560
gctcctactt tgaagagata tttgcgcgat aatatctcta atattttgcc aaatgaagtg    1620
cctggtacat cagatgacag tactgaagag ccagtaatga aaaaacgtac ttactgtact    1680
tactgcccct ctaaaataag gcgaaaggca aatgcatcgt gcaaaaaatg caaaaaagtt    1740
atttgtcgag agcataatat tgatatgtgc caaagttgtt tctgactgac taataagtat    1800
aatttgtttc tattatgtat aagttaagct aattacttat tttataatac aacatgactg    1860
tttttaaagt acaaaataag tttattttttg taaaagagag aatgtttaaa agttttgtta    1920
ctttatagaa gaaattttga gttttttgttt tttttaata aataaataaa cataaataaa    1980
ttgtttgttg aatttattat tagtatgtaa gtgtaaatat aataaaactt aatatctatt    2040
caaattaata aataaacctc gatatacaga ccgataaaac acatgcgtca attttacgca    2100
tgattatctt taacgtacgt cacaatatga ttatctttct aggg                    2144
```

<210> SEQ ID NO 10
<211> LENGTH: 2411
<212> TYPE: DNA
<213> ORGANISM: Trichoplusia ni

<400> SEQUENCE: 10

```
cattcttgaa atattgctct ctctttctaa atagcgcgaa tccgtcgctg tgcatttagg     60
acatctcagt cgccgcttgg agctcccgtg aggcgtgctt gtcaatgcgg taagtgtcac    120
tgattttgaa ctataacgac cgcgtgagtc aaaatgacgc atgattatct tttacgtgac    180
ttttaagatt taactcatac gataattata ttgttatttc atgttctact tacgtgataa    240
cttattatat atatattttc ttgttataga tatcgtgact aatatataat aaaatgggta    300
gttctttaga cgatgagcat atcctctctg ctcttctgca aagcgatgac gagcttgttg    360
gtgaggattc tgacagtgaa atatcagatc acgtaagtga agatgacgtc cagagcgata    420
cagaagaagc gtttatagat gaggtacatg aagtgcagcc aacgtcaagc ggtagtgaaa    480
tattagacga acaaaatgtt attgaacaac caggttcttc attggcttct aacagaatct    540
tgaccttgcc acagaggact attagaggta agaataaaca ttgttggtca acttcaaagt    600
ccacgaggcg tagccgagtc tctgcactga acattgtcag atctcaaaga ggtccgacgc    660
gtatgtgccg caatatatat gacccacttt tatgcttcaa actatttttt actgatgaga    720
taatttcgga aattgtaaaa tggacaaatg ctgagatatc attgaaacgt cgggaatcta    780
tgacaggtgc tacatttcgt gacacgaatg aagatgaaat ctatgctttc tttggtattc    840
tggtaatgac agcagtgaga aaagataacc acatgtccac agatgacctc tttgatcgat    900
ctttgtcaat ggtgtacgtc tctgtaatga gtcgtgatcg ttttgatttt ttgatacgat    960
```

```
gtcttagaat ggatgacaaa agtatacggc ccacacttcg agaaaacgat gtatttactc    1020
ctgttagaaa aatatgggat ctctttatcc atcagtgcat acaaaattac actccagggg    1080
ctcatttgac catagatgaa cagttacttg gttttagagg acggtgtccg tttaggatgt    1140
atatcccaaa caagccaagt aagtatgaaa taaaaatcct catgatgtgt gacagtggta    1200
cgaagtatat gataaatgga atgccttatt tgggaagagg aacacagacc aacggagtac    1260
cactcggtga atactacgtg aaggagttat caaagcctgt gcacggtagt tgtcgtaata    1320
ttacgtgtga caattggttc acctcaatcc ctttggcaaa aaacttacta caagaaccgt    1380
ataagttaac cattgtggga accgtgcgat caaacaaacg cgagataccg gaagtactga    1440
aaaacagtcg ctccaggcca gtgggaacat cgatgttttg ttttgacgga ccccttactc    1500
tcgtctcata taaaccgaag ccagctaaga tggtatactt attatcatct tgtgatgagg    1560
atgcttctat caacgaaagt accggtaaac cgcaaatggt tatgtattat aatcaaacta    1620
aaggcggagt ggacacgcta gaccaaatgt gttctgtgat gacctgcagt aggaagacga    1680
ataggtggcc tatggcatta ttgtacggaa tgataaacat tgcctgcata aattctttta    1740
ttatatacag ccataatgtc agtagcaagg gagaaaaggt tcaaagtcgc aaaaaattta    1800
tgagaaacct ttacatgagc ctgacgtcat cgtttatgcg taagcgttta gaagctccta    1860
ctttgaagag atatttgcgc gataatatct ctaatatttt gccaaatgaa gtgcctggta    1920
catcagatga cagtactgaa gagccagtaa tgaaaaaacg tacttactgt acttactgcc    1980
cctctaaaat aaggcgaaag gcaaatgcat cgtgcaaaaa atgcaaaaaa gttatttgtc    2040
gagagcataa tattgatatg tgccaaagtt gtttctgact gactaataag tataatttgt    2100
ttctattatg tataagttaa gctaattact tattttataa tacaacatga ctgtttttaa    2160
agtacaaaat aagtttattt ttgtaaaaga gagaatgttt aaaagttttg ttactttata    2220
gaagaaattt tgagtttttg ttttttttta ataaataaat aaacataaat aaattgtttg    2280
ttgaatttat tattagtatg taagtgtaaa tataataaaa cttaatatct attcaaatta    2340
ataaataaac ctcgatatac agaccgataa aacacatgcg tcaattttac gcatgattat    2400
ctttaacgta c                                                         2411

<210> SEQ ID NO 11
<211> LENGTH: 679
<212> TYPE: DNA
<213> ORGANISM: Trichoplusia ni

<400> SEQUENCE: 11
ccctagaaag atagtctgcg taaaattgac gcatgcattc ttgaaatatt gctctctctt      60
tctaaatagc gcgaatccgt cgctgtgcat ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatcttttac gtgactttta agatttaact catacgataa     240
ttatattgtt atttcatgtt ctacttacgt gataacttat tatatatata tttcttgtt      300 atagatatcg tgactaatat ataataaaat gggtagttct ttagacgatg agcatatcct     360
ctctgctctt ctgcaaagcg atgacgagct tgttggtgag gattctgaca gtgaaatatc     420
agatcacgta agtgaagatg acgtccagag cgatacagaa gaagcgttta tagatgaggt     480
acatgaagtg cagccaacgt caagcggtag tgaaatatta gacgaacaaa atgttattga     540
acaaccaggt tcttcattgg cttctaacag aatcttgacc ttgccacaga ggactattag     600
aggtaagaat aaacattgtt ggtcaacttc aaagtccacg aggcgtagcc gagtctctgc     660
```

-continued

```
actgaacatt gtcagatct                                                679
```

<210> SEQ ID NO 12
<211> LENGTH: 774
<212> TYPE: DNA
<213> ORGANISM: Trichoplusia ni

<400> SEQUENCE: 12

```
ctgcagtagg aagacgaata ggtggcctat ggcattattg tacggaatga taaacattgc    60
ctgcataaat tcttttatta tatacagcca taatgtcagt agcaagggag aaaaggttca   120
aagtcgcaaa aaatttatga gaaacctttta catgagcctg acgtcatcgt ttatgcgtaa   180
gcgtttagaa gctcctactt tgaagagata tttgcgcgat aatatctcta atattttgcc   240
aaatgaagtg cctggtacat cagatgacag tactgaagag ccagtaatga aaaaacgtac   300
ttactgtact tactgcccct ctaaaataag gcgaaaggca aatgcatcgt gcaaaaaatg   360
caaaaaagtt atttgtcgag agcataaatat tgatatgtgc caaagttgtt tctgactgac   420
taataagtat aatttgtttc tattatgtat aagttaagct aattacttat tttataatac   480
aacatgactg tttttaaagt acaaataag tttattttg taaagagag aatgtttaaa   540
agttttgtta ctttatagaa gaaattttga gttttgtttt tttttaata aataaataaa   600
cataaataaa ttgtttgttg aatttattat tagtatgtaa gtgtaaatat aataaaactt   660
aatatctatt caaattaata aataaacctc gatatacaga ccgataaaac acatgcgtca   720
attttacgca tgattatctt taacgtacgt cacaatatga ttatctttct aggg          774
```

<210> SEQ ID NO 13
<211> LENGTH: 17
<212> TYPE: DNA
<213> ORGANISM: Trichoplusia ni

<400> SEQUENCE: 13

```
gtaaccctag aaagata                                                   17
```

<210> SEQ ID NO 14
<211> LENGTH: 17
<212> TYPE: DNA
<213> ORGANISM: Trichoplusia ni

<400> SEQUENCE: 14

```
gtaaccctag aaagata                                                   17
```

<210> SEQ ID NO 15
<211> LENGTH: 31
<212> TYPE: DNA
<213> ORGANISM: Trichoplusia ni

<400> SEQUENCE: 15

```
gcgcgccacc atgggtagtt ctttagacga t                                   31
```

<210> SEQ ID NO 16
<211> LENGTH: 33
<212> TYPE: DNA
<213> ORGANISM: Trichoplusia ni

<400> SEQUENCE: 16

```
gcccgtctag attagtcagt cagaaacaac ttt                                 33
```

<210> SEQ ID NO 17

```
<211> LENGTH: 33
<212> TYPE: DNA
<213> ORGANISM: Trichoplusia ni

<400> SEQUENCE: 17
atgcgcgcca ccatgggtag ttctttagac gat                               33

<210> SEQ ID NO 18
<211> LENGTH: 27
<212> TYPE: DNA
<213> ORGANISM: Trichoplusia ni

<400> SEQUENCE: 18
tatgtcgact ttaaccctag aaagata                                      27

<210> SEQ ID NO 19
<211> LENGTH: 17
<212> TYPE: DNA
<213> ORGANISM: Trichoplusia ni

<400> SEQUENCE: 19
ttaaccctag aaagata                                                 17

<210> SEQ ID NO 20
<211> LENGTH: 19
<212> TYPE: DNA
<213> ORGANISM: Trichoplusia ni

<400> SEQUENCE: 20
gtcgacttta accctagaa                                               19

<210> SEQ ID NO 21
<211> LENGTH: 17
<212> TYPE: DNA
<213> ORGANISM: Trichoplusia ni

<400> SEQUENCE: 21
ttaaccctag aaagata                                                 17

<210> SEQ ID NO 22
<211> LENGTH: 19
<212> TYPE: DNA
<213> ORGANISM: Trichoplusia ni

<400> SEQUENCE: 22
gtcgacttta accctagaa                                               19
```

MINIMAL PIGGYBAC VECTORS FOR GENOME INTEGRATION

CROSS REFERENCE TO RELATED APPLICATION

The present application is a national phase entry under 35 U.S.C. §371 of International Application No. PCT/US2014/046366, filed Jul. 11, 2014, published in English, which claims priority from U.S. Provisional Application No. 61/845,652, filed Jul. 12, 2013, all of which are incorporated herein by reference.

STATEMENT REGARDING FEDERALLY SPONSORED RESEARCH OR DEVELOPMENT

The invention was developed in part by Grant-in-Aid awards from the Greater SouthEast Affiliate of the American Heart Association (12GRNT12070291 and 09GRNT2260914). Therefore, the Government has certain rights in the invention.

INCORPORATION BY REFERENCE OF MATERIAL IN ASCII TEXT FILE

This application incorporates by reference the Sequence Listing contained in the following ASCII text file:
a) File name: SequenceListing.txt; created Mar. 8, 2017, 27 KB in size.

BACKGROUND OF THE INVENTION

Typical methods for introducing DNA into a cell include DNA condensing reagents such as calcium phosphate, polyethylene glycol, lipid-containing reagents, such as liposomes, multi-lamellar vesicles, as well as virus-mediated strategies. However, such methods can have certain limitations. For example, there are size constraints associated with DNA condensing reagents and virus-mediated strategies. Further, the amount of nucleic acid that can be delivered into a cell is limited in virus strategies. Not all methods facilitate insertion of the delivered nucleic acid into cellular nucleic acid, and while DNA condensing methods and lipid-containing reagents are relatively easy to prepare, the insertion of nucleic acid into viral vectors can be labor intensive. Virus-mediated strategies can be cell-type or tissue-type specific, and the use of virus-mediated strategies can create immunologic problems when used in vivo.

Transposons have become a suitable tool to address these issues. Transposons, or transposable elements, include a nucleic acid sequence flanked by upstream and downstream, with terminal domain sequences. Active transposons encode enzymes that facilitate the excision and insertion of the nucleic acid into target DNA sequences.

Transposable elements represent a substantial fraction of many eukaryotic genomes. For example, about 50% of the human genome is derived from transposable element sequences, and other genomes, for example plants, may consist of substantially higher proportions of transposable element-derived DNA. Transposable elements are typically divided into two classes, class 1 and class 2. Class 1 is represented by the retrotransposons (LINEs, SINEs, LTRs, and ERVs). Class 2 includes the "cut-and-paste" DNA transposons, which are characterized by terminal inverted repeats (TIRs) and are mobilized by an element-encoded transposase. Currently, 10 superfamilies of cut-and-paste DNA transposons are recognized in eukaryotes.

Transposon vectors are a proven and viable alternative to viral vectors for stable gene delivery (Meir et al., Chang Gung Med J 34:565-579 (2011); Li et al., J. Control Release 123:181-183 (2007); Kawakami et al., J. Pharm. Sci. 97:726-745 (2008); Nakanishi et al., Mol. Ther. 18:707-714 (2010)), and provide relative advantages from the standpoints of size and integration. Like integrated viruses, transposons deliver transgenes to target cells in vitro and in vivo where they are incorporated into the host genome. Unlike viruses they do not generate an immune response, they have a simpler genome, and are easier to handle. In addition, they can hold a significantly larger transgene insert than viruses, in some cases up to 100 kilobases (Li et al., Nucleic Acids Res; 39:e148 (2011)). These characteristics make transposons an attractive option for gene delivery.

PiggyBac vectors are one of the most active and flexible class 2 transposon systems available for the stable transfection of mammalian cells (Wilson et al., Mol. Ther. 15:139-145 (2007); Wu et al., Proc. Natl. Acad. Sci. U.S.A. 103:15008-15013 (2006)). The wild type piggyBac transposon is 2,472 base pairs in length, and is composed of two inverted minimal terminal repeats ("minTR"), two internal domain sequences ("ID") and a transposase-encoding domain (Zhuang et al., Acta Biochim. Biophys. Sin (Shanghai) 42:426-431 (2010)). Transposase catalyses the excision of the transposon from one DNA source (i.e., a delivered plasmid) and allows its subsequent re-integration into another DNA source (i.e., the host cell genome).

In the majority of piggyBac vectors, the transposase gene is removed from the transposon and replaced by transgenes of interest; the transposase is then usually delivered to the cell, typically by a separate plasmid. The minTRs and IDs are crucial for the effective integration of the transposon into the host genome and together (known as terminal domains) consist of more than 700 base pairs each (Zhuang et al., Acta. Biochim. Biophys. Sin (Shanghai) 42:426-431 (2010)). The 5' terminal domain also serves as a native promoter for transposase expression. As part of the transposition, the terminal domains are integrated into the host cell genome, exclusively at TTAA integration site, alongside the delivered transgene of interest (Elick et al., Genetica 98:33-41 (1996); Fraser et al., Insect Mol. Biol. 5:141-151 (1996)). Therefore, like integrated viruses, they deliver a significant amount of extra DNA to the target cell genome. Although the terminal domains are required for successful transposition, once integrated into the host cell genome, they perform no useful function. In fact, they may increase the risk of insertional mutagenesis (Meir et al., *BMC Biotechnol* 2011; 11:28 (2011)), due to any apparent or potential promoter or enhancer activity that the terminal domains might exert on host cell oncogenes (Cadinanos et al., *Nucleic Acids Res*. 35:e87 (2007); Shi et al., *BMC Biotechnol*. 7:5 (2007). Neither the 5' nor the 3' piggyBac minTRs contain known active promoters or enhancers (Handler et al., *Proc. Natl. Acad. Sci. USA* 95:7520-7525 (1998); Shi et al., *BMC Biotechnol*. 7:5 (2007)).

However, attempts to reduce the size of the terminal domains to decrease this risk have resulted in a significant loss of transposition efficiency. See, e.g., Zhuang et al., Acta Biochim. Biophys. Sin (Shanghai) 42:426-431 (2010); Li et al., Insect Mol. Biol. 14:17-30 (2005)).

There still remains a need for new methods and constructs for introducing DNA into a cell, and promote the efficient insertion of DNA of varying sizes into the genome of a target cell, without sacrificing stable integration efficiency and which also decreases insertional mutagenesis and eliminates promoter/enhancer activity that the integrative sequences may have on host cell oncogenes.

BRIEF SUMMARY OF THE INVENTION

Applicants have discovered that the long internal domain (ID) sequences believed to be required for the successful transposition of piggyBac vectors can be positioned elsewhere in a single vector, namely outside of the transposon (i.e., the portion of the vector that is integrated into the host cell genome), without sacrificing transposition efficiency.

Accordingly, a first aspect of the present invention is directed to a genetic delivery system, comprising: a first polynucleotide vector comprising a) a transposon flanked at its 5' and 3' ends by a TTAA sequence, wherein the transposon comprises a nucleic acid to be introduced into the genome of a target cell, and wherein the transposon further comprises piggyBac 5' and 3' inverted minimal terminal repeat sequences (minTR) that flank the nucleic acid, or variants of the minTRs, and b) a helper portion that is not delivered to the genome of the target cell, which comprises 5' and 3' piggyBac internal domain (ID) sequences, or variants thereof. The delivery system may further comprise a transposase gene operably linked to a promoter that is functional in the target cell, wherein the transposase gene expresses transposase that catalyzes excision of the nucleic acid from the vector and insertion of the nucleic acid into the genome or extrachromosomal DNA of the target cell. The transposase gene may be located on the same vector or on a different vector. In yet other embodiments, the genetic delivery system includes the transposase, which is delivered to the target cell as a protein.

A second aspect of the present invention is directed to a method of delivering nucleic acid into the genome of a target cell, comprising introducing the genetic delivery system into the target cell; and culturing the target cell transformed with the genetic delivery system under conditions in which the transposase gene is expressed such that the transposon is delivered into the genome of the target cell. In some embodiments, the target cell is an animal cell such as a stem cell. For purposes of the present invention, the genome of the target cell refers to both chromosomal and extra-chromosomal DNA.

The genetic constructs of the present invention differ from known vectors based on piggyBac elements in that most of both long terminal domains may be removed from the transposon or the delivered portion of the vector, without causing a significant loss of transposition efficiency. Only the two minTR sequences (that are recognized by a piggyBac transposase) must be present in the transposon. The vector also includes a non-delivered (i.e., helper or non-transposable) part, which in some embodiments contains the internal domains (or variants thereof), and in other embodiments, contains the internal domains and the transposase gene. The transposase gene may thus be situated on the same or a different vector. Thus, the inventive vectors include two different sets of piggyBac sequences each of which has been modified to serve different functions the fragment (transposon or delivered portion) that is delivered to the host genome is substantially truncated which decreases the amount of extra (non-encoding) DNA incorporated into the host genome while the helper (non-transposable) sequence provides the internal domains necessary for efficient transposition of the transposon.

The genetic transfer system of the present invention substantially decreases the size of the overall length of the non-essential or helper DNA within the transposon (which as shown in an exemplified embodiment, may entail a decrease from about 1,500 to just 98 base pairs) which significantly decreases the size of the overall nucleic acid integrated into the host cell genome. The large reduction in the size of the nucleic acid sequence that is incorporated into the target cell genome not only decreases the risk of insertional mutagenesis, but also eliminates any potential promoter or enhancer activity that the terminal domains might exert on host cell oncogenes. This reduction in non-essential DNA thus makes the vectors of the present invention safer and a more attractive alternative for use in human research.

BRIEF DESCRIPTION OF THE DRAWINGS

FIG. 5 (B) shows quantitative PCR (qPCR) on DNA samples from different HEK-293 cells and plasmid-166 using the inner (1) and the outer (2) primer and normalized to the inner primer (comparison control) and plasmid-166 DNA (n=3), wherein plasmid: double transposon plasmid-166 DNA; RFP(+): total DNA from HEK-293 cells stably expressing RFP; mix: mix population of RFP(+) cells 28 days post transfection; clone A, B, C: individual clones derived from mix population of RFP(+) cells 65 days post-transfection.

DETAILED DESCRIPTION

Figure 1:
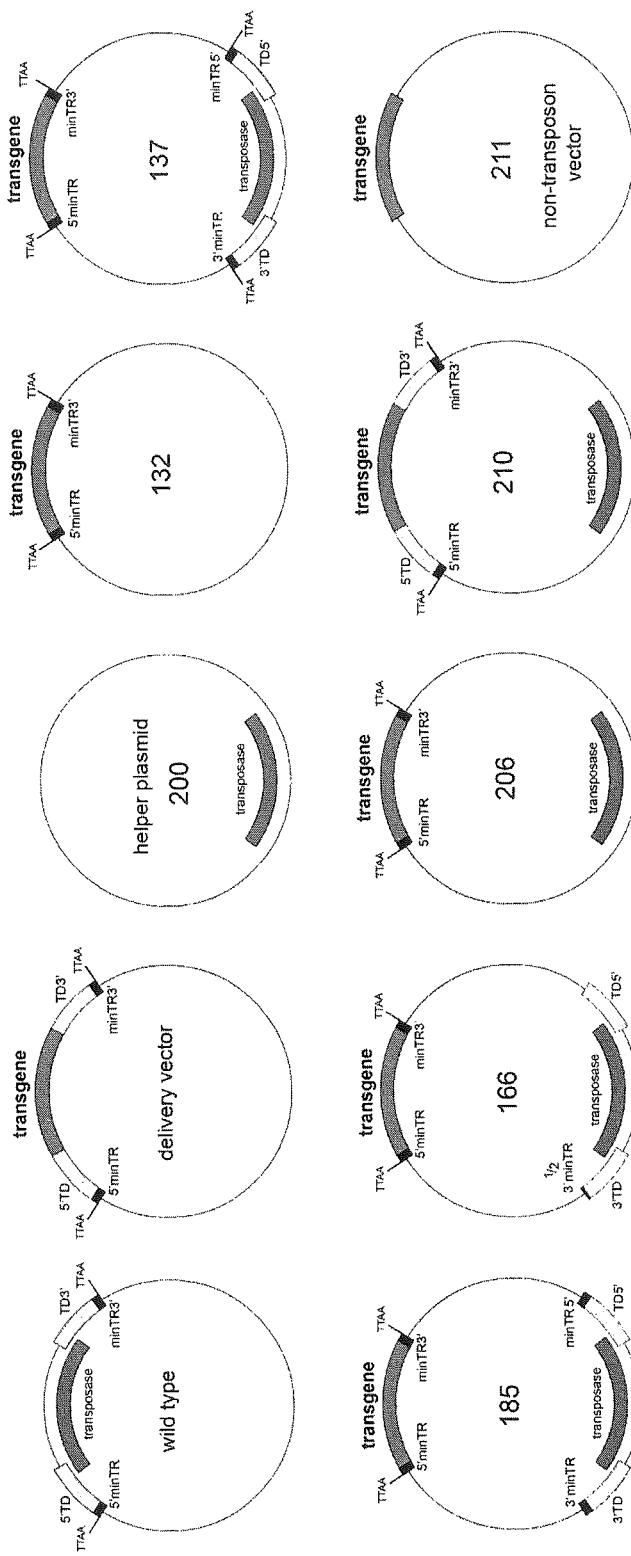
FIG. 1 shows a schematic presentation of several inventive vectors, wherein 5'TRmin, 3'TRmin: minimal 5' or 3' terminal repeats (in black); ½ 3'minTR: half of the 3' terminal repeat in plasmid-166 (in black); 5' TD, 3' TD: 5' or 3' full-length terminal domains (including the 5'TRmin or 3'TRmin) (in yellow and black); transgene: delivered gene(s), (in this paper—red fluorescent protein (RFP), (in blue)); transposase: piggyBac transposase gene (in red).

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; *Using Antibodies: A Laboratory Manual: Portable Protocol NO. I* by Edward Harlow, David Lane, Ed Harlow (1999, Cold Spring Harbor Laboratory Press, ISBN 0-87969-544-7); *Antibodies: A Laboratory Manual*, by Ed Harlow (Editor), David Lane (Editor) (1988, Cold Spring Harbor Laboratory Press, ISBN 0-87969-3, 4-2), 1855. *Handbook of Drug Screening*, edited by Ramakrishna Seethala, Prabhavathi B. Fernandes (2001, New York, N.Y., Marcel Dekker, ISBN 0-8247-0562-9); and *Lab Ref: A Handbook of Recipes, Reagents, and Other Reference Tools for Use at the Bench*, Edited Jane Roskams and Linda Rodgers, 2002, Cold Spring Harbor Laboratory, ISBN 0-87969-630-3.

As used herein, the term "transposon" (also referred to herein as the delivered portion, delivery cassette, or the transposable element) refers to a polynucleotide that is able to excise from a donor polynucleotide vector, and integrate into a target site in the genome of a target cell. The integration of the nucleic acid may be transient or it may be "stable" in that it remains present in the target cell genome for more than a transient period of time and is passed on and is present in the genome of the progeny of the target cell. As described herein, the transposon includes a nucleic acid to be introduced into the genome of a target cell (which may include a coding or non-coding sequence), and 5' and 3' flanking sequences, namely 5' and 3' piggyBac minTRs to which a member of the piggyBac family of transposases binds (or recognizes). The transposon is flanked at its 5' and 3' ends by TTAA sequences.

As used herein, the term "transposase" refers to a polypeptide that catalyzes the excision of the transposon from a donor plasmid vector and the subsequent integration of the transposon into the genome of a target or host cell. In some embodiments, the transposase is present as a polynucleotide that includes a coding sequence encoding a transposase (the transposase gene). The transposase gene may be present on the same vector that contains the transposon (i.e., in cis). In other embodiments, the transposase gene may be present on a second vector (i.e., in trans), which is also delivered to the target cell. In yet other embodiments, the transposase may be present as a polypeptide.

The 2472-nucleotide sequence of the wild-type piggyBac vector from the family Noctuidae, e.g., a *Trichoplusia ni* (Cabbage looper moth) piggyBac transposon is set forth below, and is designated herein as SEQ ID NO:1.

(SEQ ID NO: 1)
CCCTAGAAAGATAGTCTGCGTAAAATTGACGCATGCATTCTTGAAATATTGCTCTCTCTTT

CTAAATAGCGCGAATCCGTCGCTGTGCATTTAGGACATCTCAGTCGCCGCTTGGAGCTCCC

GTGAGGCGTGCTTGTCAATGCGGTAAGTGTCACTGATTTTGAACTATAACGACCGCGTGAG

TCAAAATGACGCATGATTATCTTTTACGTGACTTTTAAGATTTAACTCATACGATAATTAT

ATTGTTATTTCATGTTCTACTTACGTGATAACTTATTATATATATATTTTCTTGTTATAGA

TATCGTGACTAATATATAATAAAATGGGTAGTTCTTTAGACGATGAGCATATCCTCTCTGC

TCTTCTGCAAAGCGATGACGAGCTTGTTGGTGAGGATTCTGACAGTGAAATATCAGATCAC

GTAAGTGAAGATGACGTCCAGAGCGATACAGAAGAAGCGTTTATAGATGAGGTACATGAAG

TGCAGCCAACGTCAAGCGGTAGTGAAATATTAGACGAACAAAATGTTATTGAACAACCAGG

TTCTTCATTGGCTTCTAACAGAATCTTGACCTTGCCACAGAGGACTATTAGAGGTAAGAAT

AAACATTGTTGGTCAACTTCAAAGTCCACGAGGCGTAGCCGAGTCTCTGCACTGAACATTG

TCAGATCTCAAAGAGGTCCGACGCGTATGTGCCGCAATATATATGACCCACTTTTATGCTT

CAAACTATTTTTTACTGATGAGATAATTTCGGAAATTGTAAAATGGACAAATGCTGAGATA

TCATTGAAACGTCGGGAATCTATGACAGGTGCTACATTTCGTGACACGAATGAAGATGAAA

TCTATGCTTTCTTTGGTATTCTGGTAATGACAGCAGTGAGAAAAGATAACCACATGTCCAC

AGATGACCTCTTTGATCGATCTTTGTCAATGGTGTACGTCTCTGTAATGAGTCGTGATCGT

TTTGATTTTTTGATACGATGTCTTAGAATGGATGACAAAAGTATACGGCCCACACTTCGAG

AAAACGATGTATTTACTCCTGTTAGAAAAATATGGGATCTCTTTATCCATCAGTGCATACA

AAATTACACTCCAGGGGCTCATTTGACCATAGATGAACAGTTACTTGGTTTTAGAGGACGG

TGTCCGTTTAGGATGTATATCCCAAACAAGCCAAGTAAGTATGGAATAAAAATCCTCATGA

TGTGTGACAGTGGTACGAAGTATATGATAAATGGAATGCCTTATTTGGGAAGAGGAACACA

GACCAACGGAGTACCACTCGGTGAATACTACGTGAAGGAGTTATCAAAGCCTGTGCACGGT

AGTTGTCGTAATATTACGTGTGACAATTGGTTCACCTCAATCCCTTTGGCAAAAAACTTAC

```
TACAAGAACCGTATAAGTTAACCATTGTGGGAACCGTGCGATCAAACAAACGCGAGATACC

GGAAGTACTGAAAAACAGTCGCTCCAGGCCAGTGGGAACATCGATGTTTTGTTTTGACGGA

CCCCTTACTCTCGTCTCATATAAACCGAAGCCAGCTAAGATGGTATACTTATTATCATCTT

GTGATGAGGATGCTTCTATCAACGAAAGTACCGGTAAACCGCAAATGGTTATGTATTATAA

TCAAACTAAAGGCGGAGTGGACACGCTAGACCAAATGTGTTCTGTGATGACCTGCAGTAGG

AAGACGAATAGGTGGCCTATGGCATTATTGTACGGAATGATAAACATTGCCTGCATAAATT

CTTTTATTATATACAGCCATAATGTCAGTAGCAAGGGAGAAAAGGTTCAAAGTCGCAAAAA

ATTTATGAGAAACCTTTACATGAGCCTGACGTCATCGTTTATGCGTAAGCGTTTAGAAGCT

CCTACTTTGAAGAGATATTTGCGCGATAATATCTCTAATATTTTGCCAAATGAAGTGCCTG

GTACATCAGATGACAGTACTGAAGAGCCAGTAATGAAAAAACGTACTTACTGTACTTACTG

CCCCTCTAAAATAAGGCGAAAGGCAAATGCATCGTGCAAAAAATGCAAAAAAGTTATTTGT

CGAGAGCATAATATTGATATGTGCCAAAGTTGTTTCTGACTGACTAATAAGTATAATTTGT

TTCTATTATGTATAAGTTAAGCTAATTACTTATTTTATAATACAACATGACTGTTTTTAAA

GTACAAAATAAGTTTATTTTTGTAAAAGAGAGAATGTTTAAAAGTTTTGTTACTTTATAGA

AGAAATTTTGAGTTTTTGTTTTTTTTTAATAAATAAATAAACATAAATAAATTGTTTGTTG

AATTTATTATTAGTATGTAAGTGTAAATATAATAAAACTTAATATCTATTCAAATTAATAA

ATAAACCTCGATATACAGACCGATAAAACACATGCGTCAATTTTACGCATGATTATCTTTA

ACGTACGTCACAATATGATTATCTTTCTAGGG
```

Referring to SEQ ID NO:1, from 5' to 3', the 5' minimum terminal repeat (5 minTR) (intermediate shade), which includes nucleotides 1-35, inclusive, CCCTAGAAAGA-TAGTCTGCGTAAAATTGACGCATG, is designated herein as SEQ ID NO:2.

Referring to SEQ ID NO:1, the 5' internal domain (5' ID) (underscored), which includes nucleotides 36-678, inclusive, is designated SEQ ID NO:3, the sequence of which is reproduced as follows:

```
                                          (SEQ ID NO: 3)
CATTCTTGAAATATTGCTCTCTCTTTCTAAATAGCGCGAATCCGTCGCT

GTGCATTTAGGACATCTCAGTCGCCGCTTGGAGCTCCCGTGAGGCGTGC

TTGTCAATGCGGTAAGTGTCACTGATTTTGAACTATAACGACCGCGTGA

GTCAAAATGACGCATGATTATCTTTTACGTGACTTTTAAGATTTAACTC

ATACGATAATTATATTGTTATTTCATGTTCTACTTACGTGATAACTTAT

TATATATATATTTTCTTGTTATAGATATCGTGACTAATATATAATAAAA

TGGGTAGTTCTTTAGACGATGAGCATATCCTCTCTGCTCTTCTGCAAAG

CGATGACGAGCTTGTTGGTGAGGATTCTGACAGTGAAATATCAGATCAC

GTAAGTGAAGATGACGTCCAGAGCGATACAGAAGAAGCGTTTATAGATG

AGGTACATGAAGTGCAGCCAACGTCAAGCGGTAGTGAAATATTAGACGA
```

```
                                       -continued
ACAAAATGTTATTGAACAACCAGGTTCTTCATTGGCTTCTAACAGAATC

TTGACCTTGCCACAGAGGACTATTAGAGGTAAGAATAAACATTGTTGGT

CAACTTCAAAGTCCACGAGGCGTAGCCGAGTCTCTGCACTGAACATTGT

CAGATCT.
```

Referring to SEQ ID NO:1, the 5' portion of the 5' ID that does not overlap with the transposase gene is believed to include nucleotides 36-328 inclusive, and the 3' portion of the 5' ID which overlaps with the transposase gene (underscored and light shaded) is believed to include nucleotides 329-679 inclusive.

Referring to SEQ ID NO:1, the transposase gene (light shaded), which includes nucleotides 329-2113 inclusive, is designated herein as SEQ ID NO:4, the sequence of which is reproduced as follows:

```
                                          (SEQ ID NO: 4)
CAAAGAGGTCCGACGCGTATGTGCCGCAATATATATGACCCACTTTTAT

GCTTCAAACTATTTTTTACTGATGAGATAATTTCGGAAATTGTAAAATG

GACAAATGCTGAGATATCATTGAAACGTCGGGAATCTATGACAGGTGCT

ACATTTCGTGACACGAATGAAGATGAAATCTATGCTTTCTTTGGTATTC

TGGTAATGACAGCAGTGAGAAAAGATAACCACATGTCCACAGATGACCT
```

-continued
CTTTGATCGATCTTTGTCAATGGTGTACGTCTCTGTAATGAGTCGTGAT

CGTTTTGATTTTTTGATACGATGTCTTAGAATGGATGACAAAAGTATAC

GGCCCACACTTCGAGAAAACGATGTATTTACTCCTGTTAGAAAAATATG

GGATCTCTTTATCCATCAGTGCATACAAAATTACACTCCAGGGGCTCAT

TTGACCATAGATGATGGGTAGTTCTTTAGACGATGAGCATATCCTCTCT

GCTCTTCTGCAAAGCGATGACGAGCTTGTTGGTGAGGATTCTGACAGTG

AAATATCAGATCACGTAAGTGAAGATGACGTCCAGAGCGATACAGAAGA

AGCGTTTATAGATGAGGTACATGAAGTGCAGCCAACGTCAAGCGGTAGT

GAAATATTAGACGAACAAAATGTTATTGAACAACCAGGTTCTTCATTGG

CTTCTAACAGAATCTTGACCTTGCCACAGAGGACTATTAGAGGTAAGAA

TAAACATTGTTGGTCAACTTCAAAGTCCACGAGGCGTAGCCGAGTCTCT

GCACTGAACATTGTCAGATCTAACAGTTACTTGGTTTTAGAGGACGGTG

TCCGTTTAGGATGTATATCCCAAACAAGCCAAGTAAGTATGGAATAAAA

ATCCTCATGATGTGTGACAGTGGTACGAAGTATATGATAAATGGAATGC

CTTATTTGGGAAGAGGAACACAGACCAACGGAGTACCACTCGGTGAATA

CTACGTGAAGGAGTTATCAAAGCCTGTGCACGGTAGTTGTCGTAATATT

ACGTGTGACAATTGGTTCACCTCAATCCCTTTGGCAAAAAACTTACTAC

AAGAACCGTATAAGTTAACCATTGTGGGAACCGTGCGATCAAACAAACG

CGAGATACCGGAAGTACTGAAAAACAGTCGCTCCAGGCCAGTGGGAACA

TCGATGTTTTGTTTTGACGGACCCCTTACTCTCGTCTCATATAAACCGA

AGCCAGCTAAGATGGTATACTTATTATCATCTTGTGATGAGGATGCTTC

TATCAACGAAAGTACCGGTAAACCGCAAATGGTTATGTATTATAATCAA

ACTAAAGGCGGAGTGGACACGCTAGACCAAATGTGTTCTGTGATGAC.

Referring to SEQ ID NO:1, the 3' ID (underscored), which includes nucleotides 1699-2409 inclusive, is designated herein as SEQ ID NO:5, the sequence of which is reproduced as follows:

(SEQ ID NO: 5)
CTGCAGTAGGAAGACGAATAGGTGGCCTATGGCATTATTGTACGGAATG

ATAAACATTGCCTGCATAAATTCTTTTATTATATACAGCCATAATGTCA

GTAGCAAGGGAGAAAAGGTTCAAAGTCGCAAAAAATTTATGAGAAACCT

TTACATGAGCCTGACGTCATCGTTTATGCGTAAGCGTTTAGAAGCTCCT

ACTTTGAAGAGATATTTGCGCGATAATATCTCTAATATTTTGCCAAATG

AAGTGCCTGGTACATCAGATGACAGTACTGAAGAGCCAGTAATGAAAAA

ACGTACTTACTGTACTTACTGCCCCTCTAAAATAAGGCGAAAGGCAAAT

GCATCGTGCAAAAAATGCAAAAAAGTTATTTGTCGAGAGCATAATATTG

ATATGTGCCAAAGTTGTTTCTGACTGACTAATAAGTATAATTTGTTTCT

ATTATGTATAAGTTAAGCTAATTACTTATTTTATAATACAACATGACTG

TTTTTAAAGTACAAAATAAGTTTATTTTTGTAAAAGAGAGAATGTTTAA

AAGTTTTGTTACTTTATAGAAGAAATTTTGAGTTTTGTTTTTTTTAA

TAAATAAATAAACATAAATAAATTGTTTGTTGAATTTATTATTAGTATG

-continued
TAAGTGTAAATATAATAAAACTTAATATCTATTCAAATTAATAAATAAA

CCTCGATATACAGACCGATAAAACA.

Referring to SEQ ID NO:1, the 5' portion of the 3' ID that overlaps with the transposase gene (underscored and light shaded) is believed to include nucleotides 1699-2113 inclusive, and the 3' portion of the 3' ID that does not overlap with the transposase gene (underscored), is believed to include nucleotides 2114-2409 inclusive.

Referring to SEQ ID NO:1, nucleotides 36-2409, which include the 5' ID, the transposase gene and the 3' ID, is designated as SEQ ID NO:6, the sequence of which is reproduced below:

(SEQ ID NO: 6)
CCCTAGAAAGATAGTCTGCGTAAAATTGACGCATGCATTCTTGAAATAT

TGCTCTCTCTTTCTAAATAGCGCGAATCCGTCGCTGTGCATTTAGGACA

TCTCAGTCGCCGCTTGGAGCTCCCGTGAGGCGTGCTTGTCAATGCGGTA

AGTGTCACTGATTTTGAACTATAACGACCGCGTGAGTCAAAATGACGCA

TGATTATCTTTTACGTGACTTTTAAGATTTAACTCATACGATAATTATA

TTGTTATTTCATGTTCTACTTACGTGATAACTTATTATATATATATTTT

CTTGTTATAGATATCGTGACTAATATATAATAAAATGGGTAGTTCTTTA

GACGATGAGCATATCCTCTCTGCTCTTCTGCAAAGCGATGACGAGCTTG

TTGGTGAGGATTCTGACAGTGAAATATCAGATCACGTAAGTGAAGATGA

CGTCCAGAGCGATACAGAAGAAGCGTTTATAGATGAGGTACATGAAGTG

CAGCCAACGTCAAGCGGTAGTGAAATATTAGACGAACAAAATGTTATTG

AACAACCAGGTTCTTCATTGGCTTCTAACAGAATCTTGACCTTGCCACA

GAGGACTATTAGAGGTAAGAATAAACATTGTTGGTCAACTTCAAAGTCC

ACGAGGCGTAGCCGAGTCTCTGCACTGAACATTGTCAGATCTCAAAGAG

GTCCGACGCGTATGTGCCGCAATATATATGACCCACTTTTATGCTTCAA

ACTATTTTTTACTGATGAGATAATTTCGGAAATTGTAAAATGGACAAAT

GCTGAGATATCATTGAAACGTCGGGAATCTATGACAGGTGCTACATTTC

GTGACACGAATGAAGATGAAATCTATGCTTTCTTTGGTATTCTGGTAAT

GACAGCAGTGAGAAAAGATAACCACATGTCCACAGATGACCTCTTTGAT

CGATCTTTGTCAATGGTGTACGTCTCTGTAATGAGTCGTGATCGTTTTG

ATTTTTTGATACGATGTCTTAGAATGGATGACAAAAGTATACGGCCCAC

ACTTCGAGAAAACGATGTATTTACTCCTGTTAGAAAAATATGGGATCTC

TTTATCCATCAGTGCATACAAAATTACACTCCAGGGGCTCATTTGACCA

TAGATGAACAGTTACTTGGTTTTAGAGGACGGTGTCCGTTTAGGATGTA

TATCCCAAACAAGCCAAGTAAGTATGGAATAAAAATCCTCATGATGTGT

GACAGTGGTACGAAGTATATGATAAATGGAATGCCTTATTTGGGAAGAG

GAACACAGACCAACGGAGTACCACTCGGTGAATACTACGTGAAGGAGTT

ATCAAAGCCTGTGCACGGTAGTTGTCGTAATATTACGTGTGACAATTGG

TTCACCTCAATCCCTTTGGCAAAAAACTTACTACAAGAACCGTATAAGT

TAACCATTGTGGGAACCGTGCGATCAAACAAACGCGAGATACCGGAAGT

ACTGAAAAACAGTCGCTCCAGGCCAGTGGGAACATCGATGTTTTGTTTT

-continued

```
GACGGACCCCTTACTCTCGTCTCATATAAACCGAAGCCAGCTAAGATGG

TATACTTATTATCATCTTGTGATGAGGATGCTTCTATCAACGAAAGTAC

CGGTAAACCGCAAATGGTTATGTATTATAATCAAACTAAAGGCGGAGTG

GACACGCTAGACCAAATGTGTTCTGTGATGACCTGCAGTAGGAAGACGA

ATAGGTGGCCTATGGCATTATTGTACGGAATGATAAACATTGCCTGCAT

AAATTCTTTTATTATATACAGCCATAATGTCAGTAGCAAGGGAGAAAAG

GTTCAAAGTCGCAAAAAATTTATGAGAAACCTTTACATGAGCCTGACGT

CATCGTTTATGCGTAAGCGTTTAGAAGCTCCTACTTTGAAGAGATATTT

GCGCGATAATATCTCTAATATTTTGCCAAATGAAGTGCCTGGTACATCA

GATGACAGTACTGAAGAGCCAGTAATGAAAAAACGTACTTACTGTACTT

ACTGCCCCTCTAAAATAAGGCGAAAGGCAAATGCATCGTGCAAAAAATG

CAAAAAAGTTATTTGTCGAGAGCATAATATTGATATGTGCCAAAGTTGT

TTCTGACTGACTAATAAGTATAATTTGTTTCTATTATGTATAAGTTAAG

CTAATTACTTATTTTATAATACAACATGACTGTTTTTAAAGTACAAAAT

AAGTTTATTTTTGTAAAAGAGAGAATGTTTAAAAGTTTTGTTACTTTAT

AGAAGAAATTTTGAGTTTTGTTTTTTTTTAATAAATAAATAAACATAA

ATAAATTGTTTGTTGAATTTATTATTAGTATGTAAGTGTAAATATAATA

AAACTTAATATCTATTCAAATTAATAAATAAACCTCGATATACAGACCG

ATAAAACA.
```

Referring to SEQ ID NO:1, the 3' minTR (intermediate shade), which includes nucleotides 2410-2472 inclusive, is designated herein as SEQ ID NO:7, and the sequence of which is reproduced as follows:

```
                                        (SEQ ID NO: 7)
CATGCGTCAATTTTACGCATGATTATCTTTAACGTACGTCACAATATGA
TTATCTTTCTAGGG.
```

The genetic transfer system of the present invention includes at least one vector which includes a deliverable fragment, i.e., the transposon or the delivered portion that gets introduced into the genome of the target cell, and a non-delivered or helper portion or fragment. The vector may be a circular or an open (linear) plasmid, a part or entire chromatin (chromosome) from another cell, or a part of any viral vector. Any DNA can harbor a transposon and thus serve as a vector for purposes of the present invention. The delivered portion of the vector is flanked by the TTAA boxes. The deliverable portion of the vector also contains DNA (e.g., a coding sequence such as a transgene of interest, or a non-coding sequence, e.g., shRNA) flanked at its 5' and 3' ends by the minTRs, i.e., SEQ ID NOs:2 and 7, respectively. These sequences are substantially conserved among piggyBac vectors. Variants of SEQ ID NOS:2 and 7 may be useful, e.g., which differ from SEQ ID NOS:2 and 7 in terms of one or more nucleotide substitutions, insertions or deletions. For example, as reported in Li et al., Insect Mol. Biol. 14(1):17-30 (2005), the 3' minTR designated herein as SEQ ID NO:7 may be modified by at least one nucleotide substitution, e.g., nucleotide 17 ("G") may be replaced with "T", without losing transposition efficiency. Other sequences may be present in the transposon, e.g., the 5' and/or 3' IDs (e.g., SEQ ID NOS:3 and 5) or a portion thereof, may flank the 5' and 3' minTRs, respectively. Regulatory elements (e.g., expression control sequences) and additional sequences that may be present, particularly in embodiments wherein the nucleic acid includes a coding sequence, include promoters, border control elements, locus-control regions, silencers, enhancers, insulators, terminators, linkers, integration sequences, etc.

The non-delivered or helper portion or fragment of the vector includes the 5' and 3' IDs, e.g., SEQ ID NOs:3 and 5, or variants thereof. For example, the overlapping or non-overlapping portion of the 5' ID or the overlapping portion or non-overlapping portion of the 3' ID may be truncated by about 50% (e.g., from about 1, 5, 10, 15, 20, 25, 30, 35, 40, 45, or 50%) without a major effect on transposition efficiency. See, e.g., Li et al., Insect Mol. Biol. 14(1):17-30 (2005) and Zhuang, et al., Acta Biochim. Biophys. Sin. 42(6):426-31 (2010). To the extent that the non-overlapping portions of the 5' ID or the 3' ID are truncated, the deleted nucleotides are preferably relocated in the transposon and flanking their respective minTR. The 5' and 3' IDs may also be modified in terms of one or more nucleotide substitutions, insertions or deletions.

In some embodiments, the genetic transfer system includes a single vector in which the helper portion further includes the transposase gene. The single-vector genetic transfer systems of the present invention are advantageous for in vivo applications, as compared to many current transposon vectors which commonly use two-vector systems, one to deliver the transposon and a second to deliver the transposase (Nakanishi et al., Mol. Ther. 18:707-714 (2010); Wilson et al., Mol. Ther. 15:139-145 (2007); Kahlig et al., Proc. Natl. Acad. Sci. U.S.A. 107:1343-1348 (2010); Yusa et al., Nat. Methods 6:363-369 (2009)).

In these embodiments, the transposase gene may be flanked by the 5' and 3' IDs, e.g., as disclosed herein as SEQ ID NO:6, and which represents the simplest, most compact and efficient design of a single-vector genetic transfer system of the present invention. Alternatively, the transposase gene (e.g., SEQ ID NO:4) may be situated between the delivered portion and the 5' ID or between the delivered portion and the 3' ID (or between two IDs, overlap, not overlap or partially overlap with IDs). In these alternative embodiments, the 5' and 3' IDs may be immediately contiguous or separated by a linker sequence (L) that may be of variable length (e.g., 6,000 nucleotides or even more). Plainly, in these embodiments, the overlapping portions of the 5' and 3' IDs may be duplicated and be present in two distinct locations in the vector. The 5' and 3' IDs (and the transposase gene) may be present in any orientation relative to each other and to the transposon.

In other embodiments, the transposase gene may be situated on a second vector. If located on the same vector, both IDs and transposase gene may have any orientation to each other and to the delivered portion.

Due to the degeneracy of the genetic code, one or more of the wild type codons present in a piggyBac transposase gene obtained from the cabbage looper moth (SEQ ID NO:4) can be substituted with one or more synonymous codons to obtain a distinct sequence that encodes the same functional piggyBac transposase as the wild-type piggyBac transposase gene from cabbage looper moth. Depending upon the target cell, one or more codons in the coding region of the sequence may be changed by substituting codons that are more common to the organism (which is the native source of the cells) in which expression is desired than to the organism from which the sequence was originally identified in order to improve expression of the transposase gene. See, e.g., U.S. Pat. No. 5,500,365. Examples of codon-humanized sequences that encode piggyBac transposases wherein the number of codons that occur more frequently in human genes is increased relative to the coding sequence obtained from *Trichoplusia*, are known in the art. See, e.g., U.S. Patent Application Publication 2010/0240133 A1. Such humanized transposases may be may have at least 95%, 96%, 97%, 98%, or 99% sequence identity with the wild type transposase encoded by SEQ ID NO:4. Other transposase genes that differ from SEQ ID NO:4 in terms of one or more codons (and result in one or more amino acid substitutions, insertions or deletions) may also be suitable for use in the present invention, provided that the transposase recognizes the minTR sequences in the transposon and is capable of excising the nucleic acid from the vector and allowing for its insertion into the genome of the target cell.

The helper portion of the plasmid vector may contain further sequences. For example, in some embodiments, the 5' ID (or variant thereof) is flanked at its 5' end by the 5' minTR, i.e., SEQ ID NO:2, or a portion thereof. In some embodiments, the 3' ID (or variant thereof) is flanked at its 3' end by the 3' minTR, i.e., SEQ ID NO:7, or a portion thereof. In other embodiments, both the 5' and the 3' minTRs are present in the helper portion of the vector.

Figure 2:
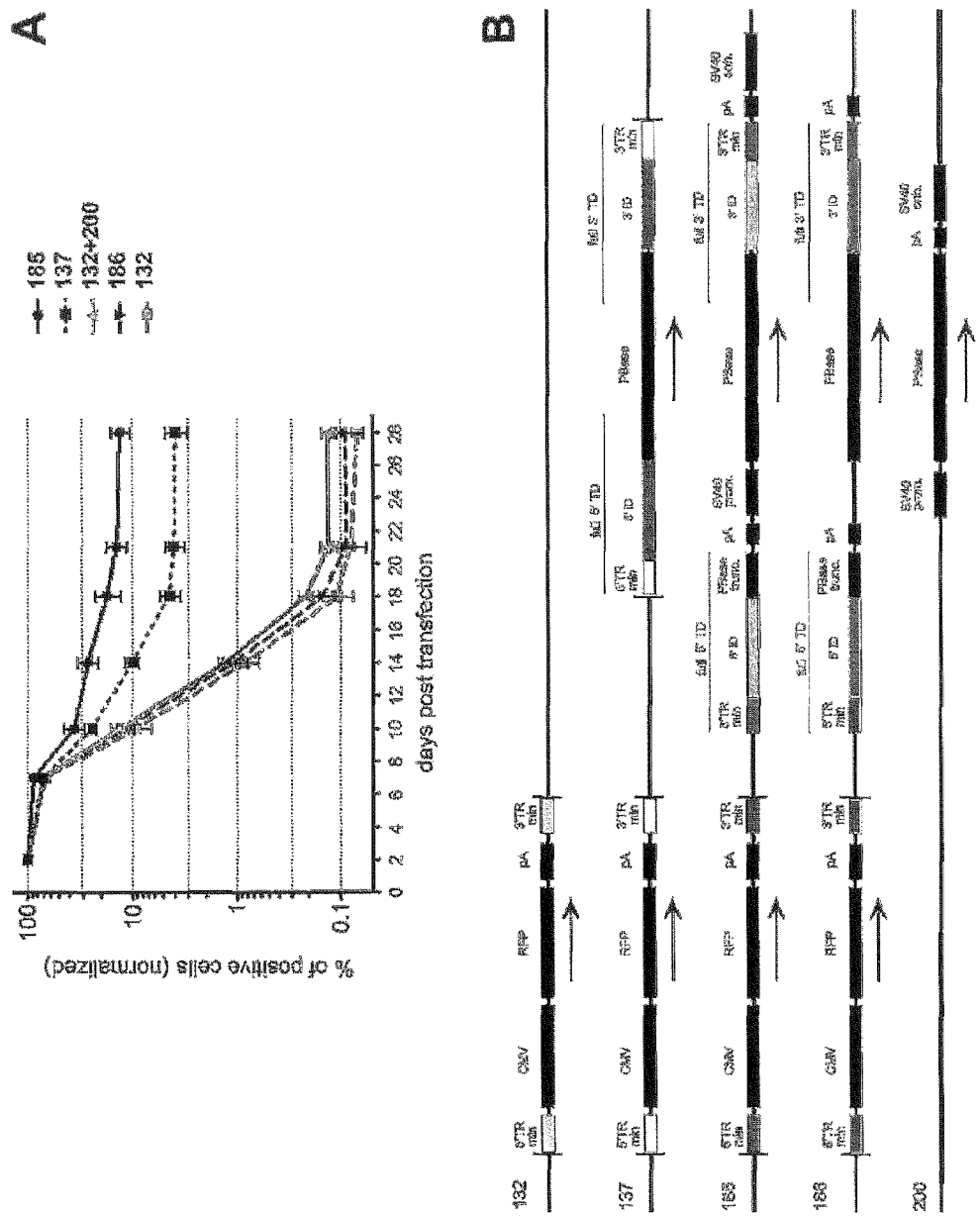
FIG. 2 (A) shows the percentage of RFP-positive HEK-293 cells after their transfection with the indicated transposon vectors (n=4); and (B) shows a detailed presentation of the tested vectors, all of which included a delivered portion or cassette that contained the reporter gene (red fluorescent protein (RFP)), flanked by 5' and 3' minTRs. 5'TRmin, 3'TRmin: minimal 5' or 3' terminal repeats (in light gray); CMV: cytomegalovirus promoter; RFP: red fluorescent protein; pA: polyadenylation signal (a SV40 polyadenylation signal for the RFP delivered cassette on the left and two structurally different (synthetic) polyadenylation signals for the helper segment in plasmids 185 and 186 on the right; and in plasmid-200); full 5' TD, full 3' TD: 5' or 3' full length terminal domains; 5'ID, 3'ID: internal 5' or 3' domains that do not overlap with the transposase gene (in gray); SV40prom and SV40enh: SV40 promoter or enhancer; PBase: piggyBac transposase gene; PBase trunc: truncated 5' piggyBac transposase gene with added stop codon in vectors 185 and 186 (this produces a truncated transposase). Black vertical lines indicate non-mutated TTAA integration sites flanking transposition-competent sequences. Arrows indicate the orientation of the operons. Prokaryotic origin of replication and ampicillin resistance gene are not shown. (Vectors are aligned for easier comparison, but distances between delivered cassette and the helper part of the plasmid are not drawn to scale).
Figure 7:
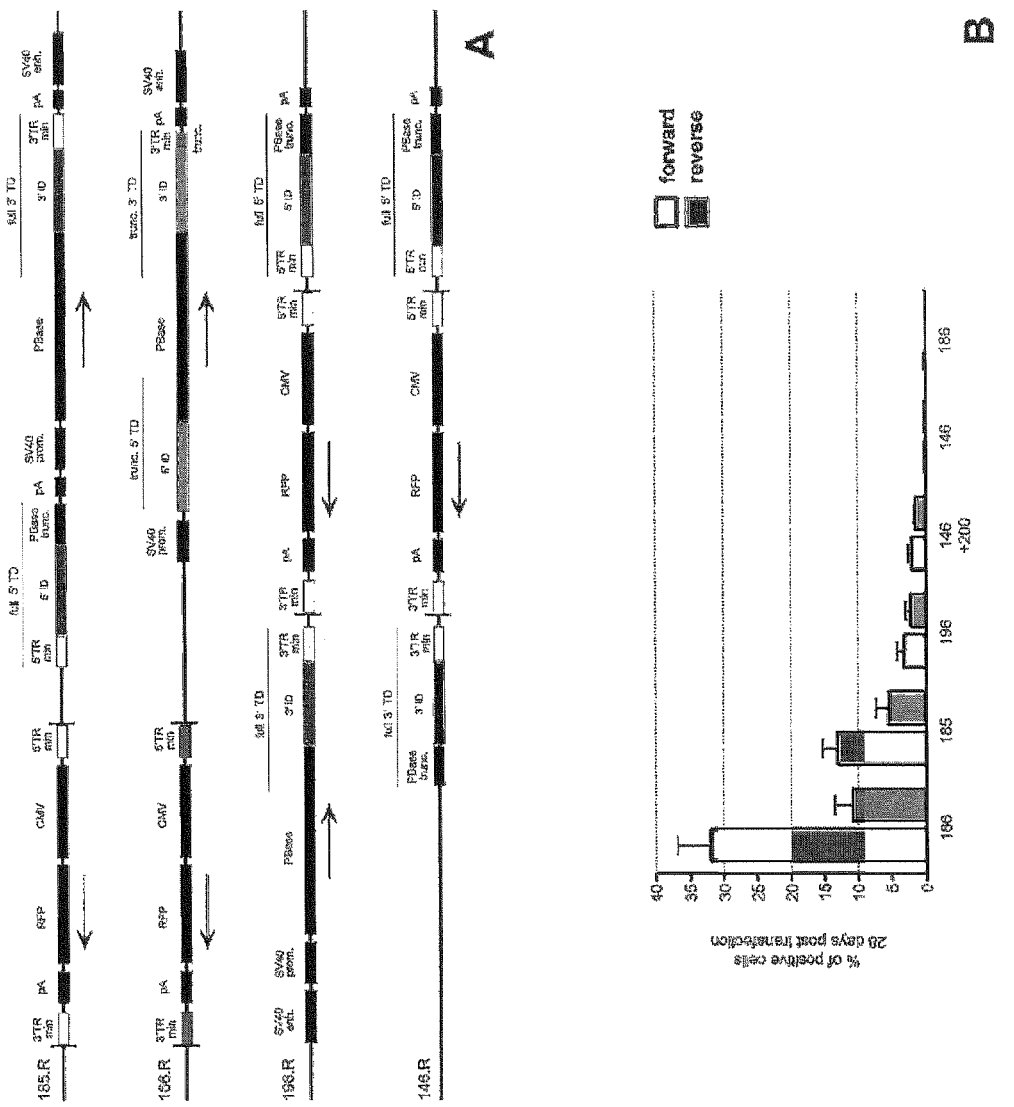
FIG. 7(A) shows linear maps of 4 inventive vectors (plasmids 146R, 166R, 185R, and 196R); wherein 5'TRmin, 3'TRmin: minimal 5' or 3' terminal repeats (in light gray); 3'TRmin trunc.: internal 37 bp fragment of 3' minimal terminal repeat in helper part of plasmid-166R (in light gray); CMV: cytomegalovirus promoter; RFP: red fluorescent protein; pA: polyadenylation signal (SV40 polyadenylation signal for the RFP delivered cassette and a synthetic polyadenylation signal for helper segment); 5'ID, 3'ID: internal 5' or 3' repeats that do not overlap with the transposase gene (in gray); SV40prom and SV40enh: SV40 promoter or enhancer; PBase: piggyBac transposase gene; full 5' TD, full 3' TD: 5' or 3' full length terminal domains; PBase trunc: truncated 5' piggyBac transposase gene with added stop codon in plasmid-196R and -146R (produces truncated transposase) and 3' truncated variant in plasmid-146R (no product); trunc.5'TD, trunc.3'TD: truncated 5' terminal domain by deletion of 5' minimal terminal repeat and truncated 3' terminal domain by deletion of terminal 26 bp fragment (terminal part of 3' minimal terminal repeat) in plasmid-166R. Black vertical lines indicate non-mutated TTAA integration sites flanking transposition-competent sequences. Arrows indicate the orientation of the operons. Prokaryotic origin of replication and ampicillin resistance gene are not shown. (Vectors are aligned for easier comparison, but distances between delivered cassette and helper part of plasmid are not drawn to scale)
FIG. 7(B) shows the percentage of RFP(+) HEK-293 cells after their transfection with the indicated transposon vectors (n=4).)

Thus, by way of example, the nucleotide sequences for the 5' and the 3' portions of the helper domain of vectors 185 and 185R, illustrated herein as FIGS. 2 and 7, are set forth below and designated herein as SEQ ID NOs:8 and 9:

```
                                               (SEQ ID NO: 8)
CCCTAGAAAGATAGTCTGCGTAAAATTGACGCATGCATTCTTGAAATAT

TGCTCTCTCTTTCTAAATAGCGCGAATCCGTCGCTGTGCATTTAGGACA

TCTCAGTCGCCGCTTGGAGCTCCCGTGAGGCGTGCTTGTCAATGCGGTA

AGTGTCACTGATTTTGAACTATAACGACCGCGTGAGTCAAAATGACGCA

TGATTATCTTTTACGTGACTTTTAAGATTTAACTCATACGATAATTATA

TTGTTATTTCATGTTCTACTTACGTGATAACTTATTATATATATATTTT

CTTGTTATAGATATCGTGACTAATATATAATAAAATGGGTAGTTCTTTA

GACGATGAGCATATCCTCTCTGCTCTTCTGCAAAGCGATGACGAGCTTG

TTGGTGAGGATTCTGACAGTGAAATATCAGATCACGTAAGTGAAGATGA

CGTCCAGAGCGATACAGAAGAAGCGTTTATAGATGAGGTACATGAAGTG

CAGCCAACGTCAAGCGGTAGTGAAATATTAGACGAACAAAATGTTATTG

AACAACCAGGTTCTTCATTGGCTTCTAACAGAATCTTGACCTTGCCACA

GAGGACTATTAGAGGTAAGAATAAACATTGTTGGTCAACTTCAAAGTCC

ACGAGGCGTAGCCGAGTCTCTGCACTGAACATTGTCAGATCT;
                                               (SEQ ID NO: 9)
ATGGGTAGTTCTTTAGACGATGAGCATATCCTCTCTGCTCTTCTGCAAA

GCGATGACGAGCTTGTTGGTGAGGATTCTGACAGTGAAATATCAGATCA

CGTAAGTGAAGATGACGTCCAGAGCGATACAGAAGAAGCGTTTATAGAT

GAGGTACATGAAGTGCAGCCAACGTCAAGCGGTAGTGAAATATTAGACG

AACAAAATGTTATTGAACAACCAGGTTCTTCATTGGCTTCTAACAGAAT

CTTGACCTTGCCACAGAGGACTATTAGAGGTAAGAATAAACATTGTTGG

TCAACTTCAAAGTCCACGAGGCGTAGCCGAGTCTCTGCACTGAACATTG
```

```
                                               -continued
TCAGATCTCAAAGAGGTCCGACGCGTATGTGCCGCAATATATATGACCC

ACTTTTATGCTTCAAACTATTTTTTACTGATGAGATAATTTCGGAAATT

GTAAAATGGACAAATGCTGAGATATCATTGAAACGTCGGGAATCTATGA

CAGGTGCTACATTTCGTGACACGAATGAAGATGAAATCTATGCTTTCTT

TGGTATTCTGGTAATGACAGCAGTGAGAAAAGATAACCACATGTCCACA

GATGACCTCTTTGATCGATCTTTGTCAATGGTGTACGTCTCTGTAATGA

GTCGTGATCGTTTTGATTTTTTGATACGATGTCTTAGAATGGATGACAA

AAGTATACGGCCCACACTTCGAGAAAACGATGTATTTACTCCTGTTAGA

AAAATATGGGATCTCTTTATCCATCAGTGCATACAAAATTACACTCCAG

GGGCTCATTTGACCATAGATGAACAGTTACTTGGTTTTAGAGGACGGTG

TCCGTTTAGGATGTATATCCCAAACAAGCCAAGTAAGTATGGAATAAAA

ATCCTCATGATGTGTGACAGTGGTACGAAGTATATGATAAATGGAATGC

CTTATTTGGGAAGAGGAACACAGACCAACGGAGTACCACTCGGTGAATA

CTACGTGAAGGAGTTATCAAAGCCTGTGCACGGTAGTTGTCGTAATATT

ACGTGTGACAATTGGTTCACCTCAATCCCTTTGGCAAAAAACTTACTAC

AAGAACCGTATAAGTTAACCATTGTGGGAACCGTGCGATCAAACAAACG

CGAGATACCGGAAGTACTGAAAAACAGTCGCTCCAGGCCAGTGGGAACA

TCGATGTTTTGTTTTGACGGACCCCTTACTCTCGTCTCATATAAACCGA

AGCCAGCTAAGATGGTATACTTATTATCATCTTGTGATGAGGATGCTTC

TATCAACGAAAGTACCGGTAAACCGCAAATGGTTATGTATTATAATCAA

ACTAAAGGCGGAGTGGACACGCTAGACCAAATGTGTTCTGTGATGACCT

GCAGTAGGAAGACGAATAGGTGGCCTATGGCATTATTGTACGGAATGAT

AAACATTGCCTGCATAAATTCTTTTATTATATACAGCCATAATGTCAGT

AGCAAGGGAGAAAAGGTTCAAAGTCGCAAAAAATTTATGAGAAACCTTT

ACATGAGCCTGACGTCATCGTTTATGCGTAAGCGTTTAGAAGCTCCTAC

TTTGAAGAGATATTTGCGCGATAATATCTCTAATATTTTGCCAAATGAA

GTGCCTGGTACATCAGATGACAGTACTGAAGAGCCAGTAATGAAAAAAC

GTACTTACTGTACTTACTGCCCCTCTAAAATAAGGCGAAAGGCAAATGC

ATCGTGCAAAAAATGCAAAAAAGTTATTTGTCGAGAGCATAATATTGAT

ATGTGCCAAAGTTGTTTCTGACTGACTAATAAGTATAATTTGTTTCTAT

TATGTATAAGTTAAGCTAATTACTTATTTTATAATACAACATGACTGTT

TTTAAAGTACAAAATAAGTTTATTTTTGTAAAAGAGAGAATGTTTAAAA

GTTTTGTTACTTTATAGAAGAAATTTTGAGTTTTTGTTTTTTTTAATA

AATAAATAAACATAAATAAATTGTTTGTTGAATTTATTATTAGTATGTA

AGTGTAAATATAATAAAACTTAATATCTATTCAAATTAATAAATAAACC

TCGATATACAGACCGATAAAACACATGCGTCAATTTTACGCATGATTAT

CTTTAACGTACGTCACAATATGATTATCTTTCTAGGG.
```

SEQ ID NO:8 includes, from 5' to 3', the 5' minTR (i.e., SEQ ID NO:2) and the 5' ID (i.e., SEQ ID NO:3). The 3' portion of the helper domain for vector 185, i.e., SEQ ID NO:9, contains from 5' to 3', the full-length transposase gene (i.e., SEQ ID NO:4), the non-overlapping portion of the 3' ID, and the 3' minTR (i.e., SEQ ID NO:7). Thus, in the helper domain of vector 185, the portion of the 5' ID that overlaps with the transposase gene is contained in both the 5' and 3' portions of the helper domain. These portions of the helper domain are separated by a SV40 promoter, which regulates expression of the transposase gene. Other promoters may be used, depending on the target cell.

Figure 3:
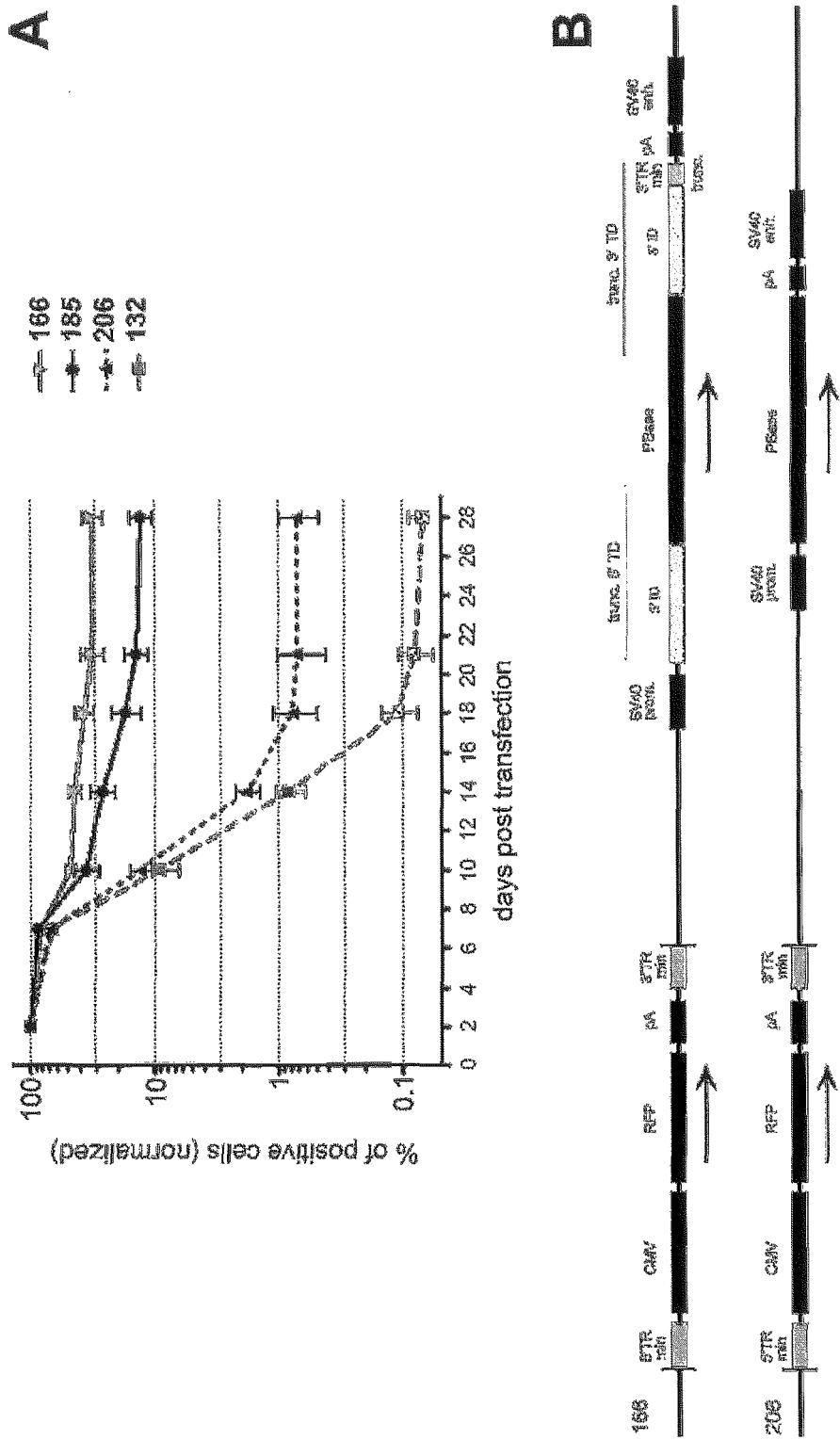
FIG. 3 (A) shows the percentage of RFP-positive HEK-293 cells after their transfection with the indicated transposon vectors (n=4); and (B) shows a detailed presentation of plasmids 166 and 206. 5'TRmin, 3'TRmin: minimal 5' or 3' terminal repeats (in light gray); 3'TRmin trunc: internal 37 base pairs fragment of 3' minimal terminal repeat in the helper part of plasmid-166 (in light gray); CMV cytomegalovirus promoter; RFP: red fluorescent protein; pA: polyadenylation signal (SV40 polyadenylation signal for the RFP delivered cassette on the left and a synthetic polyadenylation signal for helper segment on the right); 5'ID, 3'ID: internal 5' or 3' domains that do not overlap with the transposase gene (in gray); SV40prom and SV40enh: SV40 promoter and enhancer; PBase: piggyBac transposase gene; full 5' TD, full 3' TD: 5' or 3' full length terminal domains; trunc.5'TD, trunc.3'TD: truncated 5' terminal domain by deletion of 5' minimal terminal repeat and truncated 3' terminal domain by deletion of terminal 26 base pairs fragment (terminal part of 3' minimal terminal repeat) in plasmid-166. Black vertical lines indicate non-mutated TTAA integration sites flanking transposition-competent sequences. Arrows indicate the orientation of the operons. Prokaryotic origin of replication and ampicillin resistance gene are not shown. (Vectors are aligned for easier comparison, but distances between delivered cassette and helper part of plasmid are not drawn to scale).

By way of another non-limiting example, the helper portion of vectors 166 and 166R, schematically illustrated herein as FIGS. 3 and 7, has a nucleotide sequence, as set forth below, and which is designated herein as SEQ ID NO:10:

```
                                              (SEQ ID NO: 10)
CATTCTTGAAATATTGCTCTCTCTTTCTAAATAGCGCGAATCCGTCGCT

GTGCATTTAGGACATCTCAGTCGCCGCTTGGAGCTCCCGTGAGGCGTGC

TTGTCAATGCGGTAAGTGTCACTGATTTTGAACTATAACGACCGCGTGA

GTCAAAATGACGCATGATTATCTTTTACGTGACTTTTAAGATTTAACTC

ATACGATAATTATATTGTTATTTCATGTTCTACTTACGTGATAACTTAT

TATATATATATTTTCTTGTTATAGATATCGTGACTAATATATAATAAAA

TGGGTAGTTCTTTAGACGATGAGCATATCCTCTCTGCTCTTCTGCAAAG

CGATGACGAGCTTGTTGGTGAGGATTCTGACAGTGAAATATCAGATCAC

GTAAGTGAAGATGACGTCCAGAGCGATACAGAAGAAGCGTTTATAGATG

AGGTACATGAAGTGCAGCCAACGTCAAGCGGTAGTGAAATATTAGACGA

ACAAAATGTTATTGAACAACCAGGTTCTTCATTGGCTTCTAACAGAATC

TTGACCTTGCCACAGAGGACTATTAGAGGTAAGAATAAACATTGTTGGT

CAACTTCAAAGTCCACGAGGCGTAGCCGAGTCTCTGCACTGAACATTGT

CAGATCTCAAAGAGGTCCGACGCGTATGTGCCGCAATATATATGACCCA

CTTTTATGCTTCAAACTATTTTTTACTGATGAGATAATTTCGGAAATTG

TAAAATGGACAAATGCTGAGATATCATTGAAACGTCGGGAATCTATGAC

AGGTGCTACATTTCGTGACACGAATGAAGATGAAATCTATGCTTTCTTT

GGTATTCTGGTAATGACAGCAGTGAGAAAAGATAACCACATGTCCACAG

ATGACCTCTTTGATCGATCTTTGTCAATGGTGTACGTCTCTGTAATGAG

TCGTGATCGTTTTGATTTTTTGATACGATGTCTTAGAATGGATGACAAA

AGTATACGGCCCACACTTCGAGAAAACGATGTATTTACTCCTGTTAGAA

AAATATGGGATCTCTTTATCCATCAGTGCATACAAAATTACACTCCAGG

GGCTCATTTGACCATAGATGAACAGTTACTTGGTTTTAGAGGACGGTGT

CCGTTTAGGATGTATATCCCAAACAAGCCAAGTAAGTATGGAATAAAAA

TCCTCATGATGTGTGACAGTGGTACGAAGTATATGATAAATGGAATGCC

TTATTTGGGAAGAGGAACACAGACCAACGGAGTACCACTCGGTGAATAC

TACGTGAAGGAGTTATCAAAGCCTGTGCACGGTAGTTGTCGTAATATTA

CGTGTGACAATTGGTTCACCTCAATCCCTTTGGCAAAAAACTTACTACA

AGAACCGTATAAGTTAACCATTGTGGGAACCGTGCGATCAAACAAACGC

GAGATACCGGAAGTACTGAAAAACAGTCGCTCCAGGCCAGTGGGAACAT

CGATGTTTTGTTTTGACGGACCCCTTACTCTCGTCTCATATAAACCGAA

GCCAGCTAAGATGGTATACTTATTATCATCTTGTGATGAGGATGCTTCT

ATCAACGAAAGTACCGGTAAACCGCAAATGGTTATGTATTATAATCAAA

CTAAAGGCGGAGTGGACACGCTAGACCAAATGTGTTCTGTGATGACCTG

CAGTAGGAAGACGAATAGGTGGCCTATGGCATTATTGTACGGAATGATA

AACATTGCCTGCATAAATTCTTTTATTATATACAGCCATAATGTCAGTA

GCAAGGGAGAAAAGGTTCAAAGTCGCAAAAAATTTATGAGAAACCTTTA

CATGAGCCTGACGTCATCGTTTATGCGTAAGCGTTTAGAAGCTCCTACT

TTGAAGAGATATTTGCGCGATAATATCTCTAATATTTTGCCAAATGAAG

TGCCTGGTACATCAGATGACAGTACTGAAGAGCCAGTAATGAAAAAACG

TACTTACTGTACTTACTGCCCCTCTAAAATAAGGCGAAAGGCAAATGCA

TCGTGCAAAAAATGCAAAAAAGTTATTTGTCGAGAGCATAATATTGATA

TGTGCCAAAGTTGTTTCTGACTGACTAATAAGTATAATTTGTTTCTATT

ATGTATAAGTTAAGCTAATTACTTATTTTATAATACAACATGACTUTTT

TTAAAGTACAAAATAAGTTTATTTTTGTAAAAGAGAGAATGTTTAAAAG

TTTTGTTACTTTATAGAAGAAATTTTGAGTTTTTGTTTTTTTTAATAA

ATAAATAAACATAAATAAATTGTTTGTTGAATTTATTATTAGTATGTAA

GTGTAAATATAATAAAACTTAATATCTATTCAAATTAATAAATAAACCT

CGATATACAGACCGATAAAACACATGCGTCAATTTTACGCATGATTATC

TTTAACGTAC.
```

This helper domain contains from 5' to 3', SEQ ID NO:6 (which includes the 5' ID (i.e., SEQ ID NO:3), the transposase gene, and the 3' ID (i.e., SEQ ID NO:5), and a truncated version of the 3' minTR which contains 5' nucleotides 1-37 of SEQ ID NO:7. Thus, vector 166 also contains a full-length transposase gene. Vector 166 also includes an SV-40 promoter situated upstream of the helper portion, which in addition to regulating expression of the transposase gene, serves as a linker between the delivered and helper portions of the vector.

More generally, the promoter that may be present in the vector to drive expression of the transposase gene is active or functional in the target cell. In certain embodiments, this promoter is a constitutive promoter. Useful constitutive promoters include viral promoters, cellular promoters and combinations thereof. In certain embodiments, a transposase gene is operably linked to a CAG promoter that is a composite promoter comprising CMV and chicken β-actin promoter elements (Niwa et al. Gene 108(2):193-9 (1991)). In other embodiments, the expression of transposase within the cell is controlled or regulated such that it occurs for desired intervals of time. Such control or regulation is achieved by operable linkage of the transposase gene to a regulatable or inducible promoter. Regulatable promoters useful for the controlled expression of transposase include, for example, promoters whose activity is regulated by steroidal compounds, doxycycline or other tetracyclin analogs, and the like.

By way of further example, a helper domain for a vector of the present invention in which the transposase gene is not situated between the 5' and 3' IDs may have a 5' portion and a 3' portion having the nucleotide sequences as set forth below:

(SEQ ID NO: 11)
CCCTAGAAAGATAGTCTGCGTAAAATTGACGCATGCATTCTTGAAATAT
TGCTCTCTCTTTCTAAATAGCGCGAATCCGTCGCTGTGCATTTAGGACA
TCTCAGTCGCCGCTTGGAGCTCCCGTGAGGCGTGCTTGTCAATGCGGTA
AGTGTCACTGATTTTGAACTATAACGACCGCGTGAGTCAAAATGACGCA
TGATTATCTTTTACGTGACTTTTAAGATTTAACTCATACGATAATTATA
TTGTTATTTCATGTTCTACTTACGTGATAACTTATTATATATATTTT
CTTGTTATAGATATCGTGACTAATATATAATAAAATGGGTAGTTCTTTA
GACGATGAGCATATCCTCTCTGCTCTTCTGCAAAGCGATGACGAGCTTG
TTGGTGAGGATTCTGACAGTGAAATATCAGATCACGTAAGTGAAGATGA
CGTCCAGAGCGATACAGAAGAAGCGTTTATAGATGAGGTACATGAAGTG
CAGCCAACGTCAAGCGGTAGTGAAATATTAGACGAACAAAATGTTATTG
AACAACCAGGTTCTTCATTGGCTTCTAACAGAATCTTGACCTTGCCACA
GAGGACTATTAGAGGTAAGAATAAACATTGTTGGTCAACTTCAAAGTCC
ACGAGGCGTAGCCGAGTCTCTGCACTGAACATTGTCAGATCT;

(SEQ ID NO: 12)
CTGCAGTAGGAAGACGAATAGGTGGCCTATGGCATTATTGTACGGAATG
ATAAACATTGCCTGCATAAATTCTTTTATTATATACAGCCATAATGTCA
GTAGCAAGGGAGAAAAGGTTCAAAGTCGCAAAAAATTTATGAGAAACCT
TTACATGAGCCTGACGTCATCGTTTATGCGTAAGCGTTTAGAAGCTCCT
ACTTTGAAGAGATATTTGCGCGATAATATCTCTAATATTTTGCCAAATG
AAGTGCCTGGTACATCAGATGACAGTACTGAAGAGCCAGTAATGAAAAA
ACGTACTTACTGTACTTACTGCCCCTCTAAAATAAGGCGAAAGGCAAAT
GCATCGTGCAAAAAATGCAAAAAAGTTATTTGTCGAGAGCATAATATTG
ATATGTGCCAAAGTTGTTTCTGACTGACTAATAAGTATAATTTGTTTCT
ATTATGTATAAGTTAAGCTAATTACTTATTTTATAATACAACATGACTG
TTTTTAAAGTACAAAATAAGTTTATTTTTGTAAAAGAGAGAATGTTTAA
AAGTTTTGTTACTTTATAGAAGAAATTTTGAGTTTTTGTTTTTTTTTAA
TAAATAAATAAACATAAATAAATTGTTTGTTGAATTTATTATTAGTATG
TAAGTGTAAATATAATAAAACTTAATATCTATTCAAATTAATAAATAAA
CCTCGATATACAGACCGATAAAACACATGCGTCAATTTTACGCATGATT
ATCTTTAACGTACGTCACAATATGATTATCTTTCTAGGG.

Figure 6:
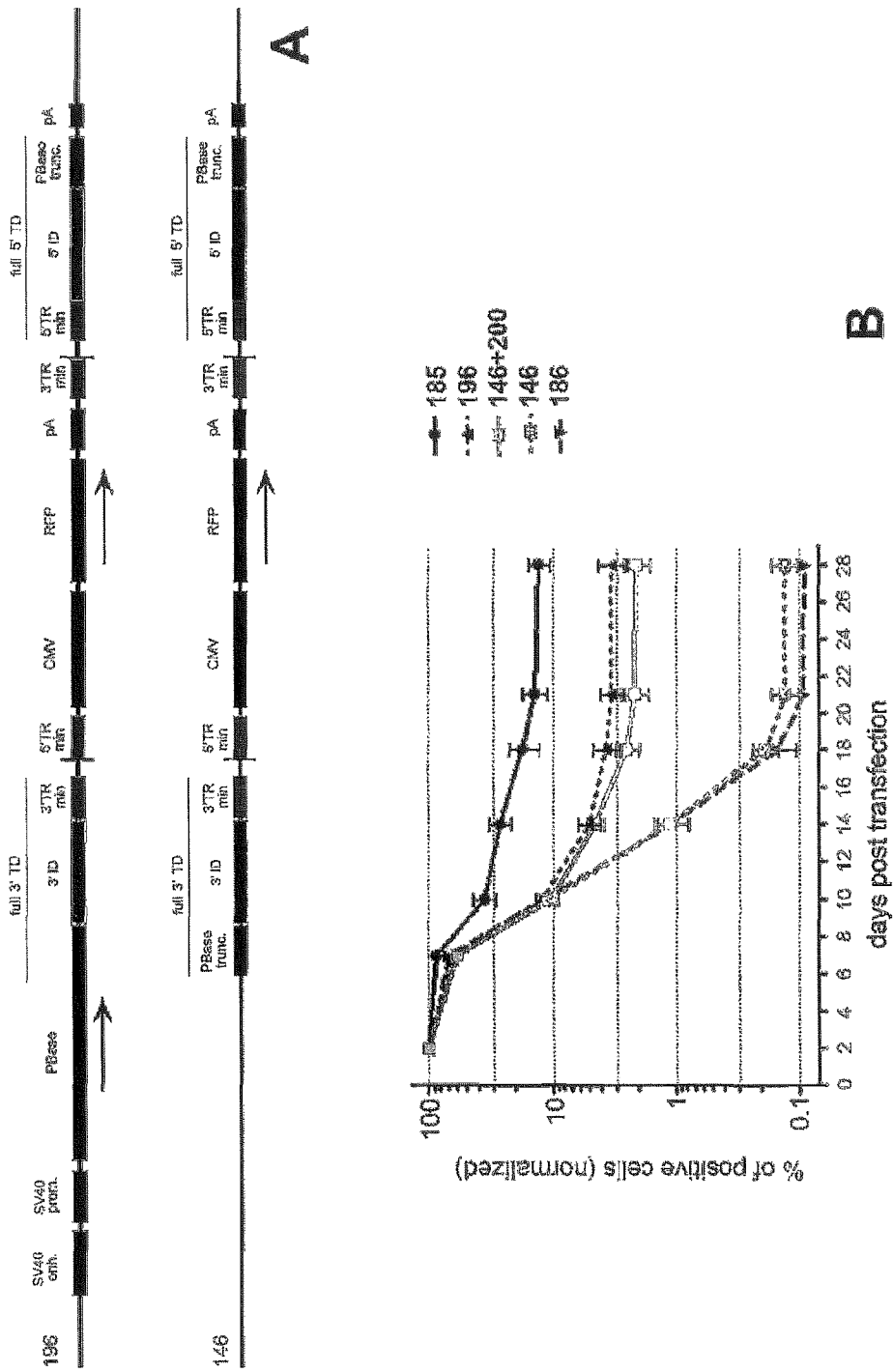
FIG. 6A shows linear maps of two inventive vectors (plasmids 146 and 196), wherein 5'TRmin, 3'TRmin: minimal 5' or 3' terminal repeats (in light gray); CMV: cytomegalovirus promoter; RFP: red fluorescent protein; pA: polyadenylation signal (SV40 polyadenylation signal for the RFP delivered cassette on the left and a synthetic polyadenylation signal for helper segment on the right); full 5' TD, full 3' TD: 5' or 3' full length terminal domains; 5'ID, 3'ID: internal 5' or 3' domains that do not overlap with the transposase gene (in gray); SV40prom and SV40enh: SV40 promoter or enhancer; PBase: piggyBac transposase gene; PBase trunc: truncated 5' piggyBac transposase gene with added stop codon in both vectors (produces truncated transposase) and 3' truncated variant in plasmid-146 (no product). Black vertical lines indicate non-mutated TTAA integration sites flanking transposition-competent sequences. Arrows indicate the orientation of the operons. Prokaryotic origin of replication and ampicillin resistance gene are not shown. (Vectors are aligned for easier comparison, but distances between delivered cassette and helper part of plasmid are not drawn to scale)
FIG. 6(B) shows the percentage of RFP(+) HEK-293 cells after their transfection with the indicated transposon vectors (n=4).

Illustrations of vectors containing such helper portions are set forth in FIGS. 6 and 7 (vector nos. 146 and 146R).

Other transposon systems containing 5' and 3' minTRs and IDs and transposase genes that may be useful in the practice of the present invention are listed in the Table below:

| suitable sources of transposon systems | | |
|---|---|---|
| Name or description | Reference | Suitable source of |
| pk[BIG-alpha] piggyBac transformation vector | Genbank Accession No. AF402295 | Transposon |
| PiggyBac helper plasmid pBlu-uTp, complete sequence | Genbank Accession No. AY196821 | Transposase |
| *Phytophthora infestans* PiggyBac-like transposon PiggyPi-1 | Genbank Accession No. AY830111 | Transposon Transposase |
| PiggyBac transformation vector pB-MCS w+ | Genbank Accession No. AY196822 | Transposon |
| PiggyBac transformation vector pB-UAS w+ | Genbank Accession No. AY196823 | Transposon |
| PiggyBac transformation vector pB-UGateway w+ | Genbank Accession No. AY196824 | Transposon |
| PiggyBac transformation vector pB-UGIR w+ | Genbank Accession No. AY196825 | Transposon |
| PiggyBac ubiquitin-transposase P replacement vector EP3005 | Genbank Accession No. AY196826 | Transposase |
| Cloning vector piggyBac . . . PB | Genbank Accession No. AY515146 | Transposon |
| Cloning vector piggyBac . . . RB | Genbank Accession No. AY515147 | Transposon |
| Cloning vector piggyBac . . . WH | Genbank Accession No. AY515148 | Transposon |
| *Heliothis virescens* transposon piggyBac transposase gene | Genbank Accession No. AY264805 | Transposase |
| More than 50 piggyBac-like sequences | Sarkar et al., 2003, Mol. Genet. Genomics 270(2): 173-80. | Transposon Transposase |
| piggyBac-like sequences in *Drosophila melanogaster* | Kapitonov & Jurka, 2003, Proc Natl Acad Sci USA 100(11): 6569-74. | Transposon Transposase |
| piggyBac-like sequences from a variety of species | Robertson, 2002, In Mobile DNA II. Craig et al., eds. (Washington, D.C., ASM Press), pp. 1093-1110 | Transposon Transposase |

The transposon and helper portions may be disposed into any vector that can be delivered (e.g., transfected) into a target cell such as an animal cell. Such vectors may include the minimal regulatory sequences necessary for the genetic transfer system to function properly in the target cell. In addition to an origin of replication, the vector may further include a marker gene such as a gene encoding for antibiotic resistance (e.g., ampicillin resistance, hygromycin resistance, neomycin resistance, etc.). Other types of marker genes encode green fluorescent protein (GFP), the blue fluorescent protein (BFP), the photo activatable-GFP (PA-GFP), the yellow shifted green fluorescent protein (Yellow GFP), the yellow fluorescent protein (YFP), the enhanced yellow fluorescent protein (EYFP), the cyan fluorescent protein (CFP), the enhanced cyan fluorescent protein (ECFP), the monomeric red fluorescent protein (mRFP1), the kindling fluorescent protein (KFP1), aequorin, the auto-fluorescent proteins (AFPs), or the fluorescent proteins JRed, TurboGFP, PhiYFP and PhiYFP-m, tHc-Red (HcRed-Tandem), PS-CFP2 and KFP-Red (all available commercially available), or other suitable fluorescent proteins chloramphenicol acetyltransferase (CAT).

The overall size of the vector is not critical, and as those skilled in the art would appreciate, is selected based on the type of vector (e.g., viral or non-viral). For example, viral vectors typically have a size ranging from about 4-11 kb, and plasmid vectors typically have a size ranging up to about 16 kb. The transposon and the helper portion of the genetic transfer system may be situated relatively closely together (e.g., separated by no more than about 17 nucleotides, or they may be spaced relatively far apart (e.g., up to about 3,000 nucleotides or more). The spacing need not be symmetrical.

The genetic transfer systems of the present invention may be used to introduce nucleic acids into any type of target cell such as an animal cell. Animal cells include both vertebrate and invertebrate animal cells (and cell lines of animal origin). Representative examples of vertebrate cells include mammalian cells including rodents (e.g., rats and mice), ungulates (e.g., cows, goats, sheep and swine) and human cells especially stem cells (e.g., pluripotent cells (i.e., a cell whose descendants can differentiate into several restricted cell types, such as hematopoietic stem cells or other stem cells), totipotent cells (i.e., a cell whose descendants can become any cell type in an organism, e.g., embryonic stem cells, and somatic stem cells e.g., hematopoietic cells). In yet other embodiments, the cells include oocytes, eggs, cells of an embryo, zygotes, sperm cells, and somatic (non-stem) mature cells from a variety of organs or tissues, such as hepatocytes, neural cells, muscle cells and blood cells (e.g., lymphocytes).

The genetic transfer systems of the present invention can be used to insert nucleic acid (e.g., DNA) into the genome of a target cell. As disclosed herein, a broad range of nucleic acids may be delivered to target cells by way of the present genetic delivery systems. Representative examples include genes encoding any polypeptide of interest, including for example, growth hormones to promote growth in a transgenic animal, or from β-galactosidase (lacZ), luciferase (LUC), and insulin-like growth factors (IGFs), α-antitrypsin, erythropoietin (EPO), factors VIII and XI of the blood clotting system, LDL-receptor, GATA-1, etc. The nucleic acid sequence further may be a suicide gene encoding e.g. apoptotic or apoptose related enzymes and genes including AIF, Apaf e.g. Apaf-1, Apaf-2, Apaf-3, or APO-2 (L), APO-3 (L), Apopain, Bad, Bak, Bax, Bcl-2, Bcl-$x_L$, Bcl-$x_S$, bik, CAD, Calpain, Caspases e.g. Caspase-1, Caspase-2, Caspase-3, Caspase-4, Caspase-5, Caspase-6, Caspase-7, Caspase-8, Caspase-9, Caspase-10, Caspase-11, or Granzyme B, ced-3, ced-9, Ceramide, c-Jun, c-Myc, CPP32, crm A, Cytochrome c, D4-GDP-DI, Daxx, CdR1, DcR1, DD, DED, DISC, DNA-$PK_{CS}$, DR3, DR4, DR5, FADD/MORT-1, FAK, Fas, Fas-ligand CD95/fas (receptor), FLICE/MACH, FLIP, Fodrin, fos, G-Actin, Gas-2, Gelsolin, glucocorticoid/glucocorticoid receptor, granzyme A/B, hnRNPs C1/C2, ICAD, ICE, JNK, Lamin A/B, MAP, MCL-1, Mdm-2, MEKK-1, MORT-1, NEDD, NF-κB, NuMa, p53, PAK-2, PARP, Perforin, PITSLRE, PKC-delta, pRb, Presenilin, prICE, RAIDD, Ras, RIP, Sphingomyelinase, SREBPs, thymidine kinase from Herpes simplex, TNF-α, TNF-α receptor, TRADD, TRAF2, TRAIL-R1, TRAIL-R2, TRAIL-R3, Transglutaminase, U1 70 kDa snRNP, YAMA, etc. The nucleic acid may include a detectable marker gene such as GFP or an affinity tag, flanked by exon splicing donor and acceptor sites. The length of the nucleic acid is not critical.

The nucleic acid to be delivered to the target cell does not necessarily include a coding sequence. Non-coding sequences such as shRNA, promoters, enhancers, sequences to mark DNA (e.g., for antibody recognition), PCR amplification sites, sequences that define restriction enzyme sites, site-specific recombinase recognition sites, sequences that are recognized by a protein that binds to and/or modifies nucleic acids, and linkers, may be included in the transposon.

In some embodiments, the nucleic acid contains a sequence encoding a gene product that alters the developmental fate of a pluripotent stem cell. For example, expression of the transcription factor Oct4 is known to be involved in maintaining embryonic stem cells in an undifferentiated state. Disruption of Oct4 expression can result in stem cell differentiation. Thus, in these embodiments, the present invention provides for an exogenous nucleic acid insertion sequence encoding a gene product that inhibits Oct4 expression. Inhibitory gene products include, for example, an antisense nucleic acid sequence or an inhibitory RNA sequence such as a shRNA or siRNA.

Differentiation of a pluripotent stem cell may be further guided to drive differentiation of the cell towards a desired cell fate. In some embodiments, the exogenous nucleic acid insertion sequence includes a sequence encoding a gene product that drives differentiation of a pluripotent cell towards a desired cell fate. For example, in some embodiments, the exogenous nucleic acid insertion sequence encodes a Sox1 protein which as known in the art can drive a cell towards a neural cell fate. Inhibition of expression of certain genes, such as Oct4, Gata6, Brachyury, and Cdx2 is also known to drive a cell towards a neural cell fate. Thus, in another illustrative example, one or more of the gene products encoded by the exogenous DNA insertion sequence comprise inhibitory gene products that inhibit expression of at least one or all of an Oct4, a Gata6, a Brachyury, or a Cdx2 gene. Inhibitory gene products that may be contained in the exogenous nucleic acid insertion sequence include, for example, antisense nucleic acids and inhibitory RNAs shRNA and siRNA. In some embodiments, the nucleic acid sequence includes a combination of a protein-encoding gene and an inhibitory nucleic acid. In some embodiments, these genes are operably linked to and under the regulatory control of an inducible promoter or regulatory system so that expression of the gene products is inducible when desired.

Methods of obtaining a cell with a genome containing the integrated nucleic acid can include the step of introducing the genetic delivery system into a target cell. As used herein, "introducing" refers to any method whereby the genetic delivery system is delivered into the cell. In some embodiments, as described herein, a cell can be transfected with a single vector that includes the transposon and a helper portion thereof that contains a transposase gene. In some other embodiments, as described herein, the transposon and the transposase gene are situated on separate vectors, in which case they are co-introduced into the target cell. The genetic delivery systems of the present invention can be introduced into a cell through a variety of standard techniques including, for example, chemical transfection, liposome-mediated transfection, microinjection, microprojectile-mediated delivery, viral mediated delivery, electroporation and nucleofection. Introduction of exogenous DNA into stem cells is reported in Kobayashi, Birth Defects Res. C Embryo Today 75(1):10-8 (2005)). Introduction of exogenous DNA into stem cells by nucleofection has been reported in Lakshmipathy, Methods Mol. Biol. 407:115-26 (2007)). The transposase can be introduced into the target cell by any suitable method, including for example, microinjection, electroporation, and membrane permeabilization (whereby cells are treated with detergents or bacterial exotoxins or other agents that form pores in the plasma membranes of animal cells).

Isolating a cell into which the transposon has integrated into a genomic sequence of the cell can also be performed in accordance with standard techniques. For example, a cell comprising a DNA insert can express a visible marker, such as a fluorescent protein or other reporter protein, encoded by the sequence of the insert that aids in the identification and isolation of a cell or cells comprising the DNA insert. A cell including a DNA insertion sequence can also express a selectable marker from the insert. Survival of the cell under certain conditions, for example exposure to a cytotoxic substance or the lack of a nutrient or substrate ordinarily required for survival, is dependent on expression or lack of expression of a selectable marker. Thus, survival or lack of survival of cells under such conditions allows for identification and isolation cells or colonies of cells that contain a nucleic acid. Cells containing a nucleic acid can also be isolated by examining the nucleic acid sequence of the host cell, such as by Southern Blotting or PCR analysis, to assay for the presence of the nucleic acid contained in the transposon. Cells from colonies that test positive for the nucleic acid can be isolated. In some cases, the expression product of a nucleic acid may produce a morphological change to the cell, such as when the expression of the exogenous sequence alters the developmental fate of the cell. Such cells can be selected based on their morphology and/or expression of one or more endogenous gene products induced by the transposon insert to obtain a cell containing a nucleic acid insert.

The invention will now be described in terms of the following non-limiting examples.

Material and Methods

Materials: Dulbecco's Modified Eagle Medium (DMEM), Dulbecco's Modified Eagle Medium/Nutrient Mixture F-12 (DMEM/F12), 0.05% trypsin/0.53 mM EDTA and L-glutamine were all purchased from Gibco (Grand Island, N.Y.). Fetal bovine serum (FBS) was purchased from Atlanta Biologicals (Lawrenceville, Ga.). FuGENE 6 and FuGENE HD Transfection Reagents were purchased from Roche Diagnostics (Indianapolis, Ind.). All restriction enzymes, DNA polymerase I (Klenow) and High Efficiency Competent E. coli Cells [NEB 10-8; Cat. No. C3019H] were from New England BioLabs (Ipswich, Mass.). Hi-Lo DNA Markers were from Minnesota Molecular, Inc. (Cat. No. 1010, Minneapolis, Minn.).

Cells: Rat pulmonary artery smooth muscle cells (PASMC) were isolated and characterized in our cell culture core (King et al., Microvasc Res. 67:139-151 (2004)). HEK-293 (Human Embryonic Kidney cell line [Cat. No. CRC-1573]), HeLa (cervical cancer derived human cells [Cat. No. CCL-2]) and L929 (murine aneuploid fibrosarcoma cell line [Cat. No. CCL-1]) were obtained from ATCC. PASMC were cultured in DMEM/F12, 10% FBS, 2 mmol L-Glutamine for up to 49 days and used for experiments at passages 4-9. Other cells were cultured in DMEM, 10% FBS, 2 mmol L-Glutamine and routinely passaged after reaching 80% confluency. All cells were grown in humidified incubators at 37° C. in 5% $CO_2$ and harvested by 0.05% trypsin/0.53 mM EDTA digestion and counted with Coulter Zl (Coulter Electronics). Counts were made in triplicate.

Vectors and delivery systems: For plasmid-132, 5' and 3' minTRs were consecutively ligated into a basic plasmid harboring prokaryotic origin of replication and ampicillin resistance gene as synthetic phosphorylated primers, forming a joined construct with two outside GTCGACT sequences containing SalI restriction enzyme site, and a single inside BclI restriction enzyme site. A CMV promoter, turboRFP, and a SV40 polyadenylation signal were added sequentially between the 5' and 3' minTRs into the BclI site yielding control plasmid-132. The plasmid harboring the wild type piggyBac, p3E1.2, (kindly gifted by Dr. A. Handler) (Handler et al., Proc. Natl. Acad. Sci. U.S.A. 95:7520-7525 (1998)) was used as a base plasmid for generating other sequences containing the transposase gene and/or piggyBac terminal domains. BssHII-BclI digestion of p3E1.2 liberated a full-length wild type piggyBac which was ligated into plasmid-132 generating a double transposon plasmid, plasmid-137. In this vector the minimal (RFP-containing) and the full-length wild type (containing transposase) piggyBac transposons were separated by 683 and 3,478-base pair linkers.

An intermediate version of a full-length piggyBac sequence (for plasmid-185) flanked with mutated integration sites (GTAA instead of TTAA) was amplified by PCR from a p3E1.2 plasmid using a single primer GTAACCCTA-GAAAGATA (SEQ ID NO:13), which served as both the forward and reverse primer. The 5' BglII digestion of this PCR-amplified wild type piggyBac in which the integration sites were mutated, produced the first part of the extended piggyBac helper sequence carrying the full length 5' terminal domain for plasmid-185 and also included a copy of the first 350 base pairs fragment of the transposase gene. This fragment was cloned into plasmid-132 downstream of the RFP delivery cassette followed by a 254-base pair linker. A synthetic polyadenylation signal and a minimal SV40 promoter were added further downstream of this sequence. The same primer, GTAACCCTAGAAAGATA (SEQ ID NO:14), paired with the reverse primer, GCGCGCCACCATGGG-TAGTTCTTTAGACGAT (SEQ ID NO:15), yielded a PCR product on p3E1.2 for the second part of the helper sequence carrying transposase gene (with an extra BssHII restriction site and a KOZAK sequence upfront) overlapped with the full-length 3' terminal domain. This part was then cloned downstream of the minimal SV40 promoter, followed by a synthetic polyadenylation signal and a SV40 enhancer to complete plasmid-185. The linker between the 3' terminal domain of the helper part and the 5' minTR of the minimal transposon was 3,354 base pairs and included the synthetic polyadenylation signal, SV40 enhancer, prokaryotic origin of replication and ampicillin resistance gene. The lengths of both linkers between the transposable and the helper parts (254 and 3,354 base pairs) were the same in plasmids 185, 186, 166, 206 and 210.

Plasmid-186 (shown in FIG. 2) was constructed similar to plasmid-185 but lacked both the SV40 minimal promoter and enhancer. The same helper sequences used for plasmid-185 were re-organized and also used in plasmid-196. The extended 5' terminal domain from plasmid-185 was cloned just downstream of the 3' minTR of the transposable (RFP-containing) unit in plasmid-196. The extended transposase gene with 3' terminal domain was cloned just upstream of the 5' minTR of the transposable unit followed by the SV40 enhancer/promoter to drive transposase expression. This vector contained only a 17 bp linker between each minTR and the long terminal domain pairs and included normal (TTAA) integration sites on the minTR side and mutated (GTAA) integration sequences on the helper's long terminal domain sides; 9 bp linkers between integration sites served as restriction enzyme site sequences. Plasmid-196 also lacked a polyadenylation signal to terminate transposase expression. Plasmid-146 was generated from plasmid 196 by simple deletion of the SV40 enhancer/promoter and most of the transposase gene up to the PstI restriction site in the piggyBac gene while retaining the 773 bp 3' terminal domain. Plasmid-146 lacked a functional transposase gene and required transposase delivery in trans. Digestion of the original wild type piggyBac plasmid p3E1.2 with SphI and BsiWI, followed by blunting of the fragment with DNA polymerase I (Klenow) resulted in a piggyBac sequence lacking an entire 5' minTR and half of the 3' minTR for the helper part of plasmid-166. The 254-base pair linker and the entire piggyBac helper part of plasmid-185 were replaced with a minimal SV40 promoter and the SphI-BsiWI truncated fragment of the wild type piggyBac transposon to complete plasmid-166. Since the native transposon promoter activity in plasmid-166 was disrupted, a minimal SV40 promoter was placed upstream of the entire helper part to drive transposase expression with extended un-translated sequence. This made the helper part of the plasmid smaller and eliminated the need for both the duplication of the 5' terminal domain and the inclusion of an extra polyadenylation signal to terminate expression of the truncated transposase (as was necessary for plasmid-185). A minimal SV40 promoter also served as a 248-base pair linker between the RFP delivered cassette and the helper sequence.

PCR amplification on plasmid p3E1.2 using the forward primer GCCCGTCTAGATTAGTCAGTCAGAAACAACTTT (SEQ ID NO:16) and the reverse primer ATGCGCGCCACCATGGGTAGTTCTTTAGACGAT (SEQ ID NO:17) resulted in the piggyBac transposase gene fragment for plasmids 206 and 210 beginning with a BssHII restriction site and the KOZAK sequence and ending with a stop codon and a XbaI restriction site at the 3' end. For plasmid-206 the piggyBac transposase gene was cloned into plasmid-166 by replacing the SphI-BsiWI truncated helper fragment. All "reverse" vectors (185R, 166R, 196R and 146R) were generated by flipping the transposable minimal piggyBac RFP delivery cassette between the two flanking SalI sites within the corresponding "forward" plasmids. SalI deletion of the transposable minimal piggyBac unit from plasmid-206 resulted in a separate helper plasmid (plasmid-200) expressing transposase which in some experiments was co-transfected with plasmids-146, -146R and -132.

Another intermediate version of the full-length piggyBac flanked with normal (TTAA) integration sites and SalI restriction enzyme sites was PCR amplified from the p3E1.2 plasmid using a single primer TATGTCGACTTTAACCCTAGAAAGATA (SEQ ID NO:18). This outermost sequence was identical to the flanking sequences of the RFP delivery cassette in all double transposon vectors and represents the site at which the delivered transposon and the non-delivered plasmid fragments join. The 5' SalI-BglII digestion of this product produced the 5' terminal domain for the transposable part of plasmid-210. The 3' PstI-SalI digestion of the same sequence liberated the 3' terminal domain for the transposable part of plasmid-210. Replacing the minTRs in the transposable part of plasmid-206 with full-length terminal domains resulted in plasmid-210. Plasmid-210 also contained the transposase gene under the control of the SV40 promoter in the helper region similar to plasmid-206.

All PCR products used for vector construction were sequenced to eliminate possible errors in amplified fragments.

qPCR: Total DNA was isolated from cells using the DNeasy Blood and Tissue kit (Qiagen, Cat. No. 69504). Identical sequences at both internal ends of the RFP delivery cassette of the vector-166 as well as their flanking (non-delivered) regions in the plasmid allowed us to use a single PCR primer with either inner or outer primers. The inner primer (TTAACCCTAGAAAGATA) (SEQ ID NO:19) was complementary to the terminal sequence of the transposon and also included the flanking TTAA integration site. The outer primer (GTCGACTTTAACCCTAGAA) (SEQ ID NO:20) straddles the TTAA integration sequence that is incorporated as part of the integrated transposon and a GTCGACT sequence that is present in the original vector, but is not incorporated into the host genome. Both primers generated a nearly identical product when tested on plasmid DNA. Differences in their ability to generate a PCR product on harvested chromatin was used to determine the integration efficiency of the transposon vector-166 by iScript SYBR Green RT-PCR kit (Bio-Rad, Cat. No. 170-8893, FIG. 5B). Regular PCR was used to show specificity of each qPCR reaction (FIG. 6A). Hi-Lo DNA Markers from Minnesota Molecular, Inc. (Cat. No. 1010, Minneapolis, Minn.) were used to identify the size of PCR products. DNA sequence analysis of all PCR products was done using multiple primers matching the internal parts of the working transposon.

Flow cytometry analysis: Cells were transiently transfected with corresponding plasmids (each expressing turboRFP with excitation/emission of 553/574 nm) using FuGENE or FuGENE HD as transfection reagents. Forty-eight (48) hours after transfection, the cells were harvested by 0.05% trypsin/0.53 mM EDTA digestion, washed, and re-suspended in cultured medium. RFP-expressing cells were sorted by BD Biosciences FACSAria cell sorter. Selected cells were re-seeded and the percentage of RFP-positive cells monitored for up to 28 days using BD Biosciences FACCantoII cell analyzer in the University of South Alabama Flow Cytometry Core.

Statistical analysis: Data are expressed as mean±SE. Changes in percentage of RFP expressing cells and qPCR data were compared using ANOVA combined with Fisher post hoc analysis, with a P value<0.05 considered significant.

Example 1—Modified piggyBac Vectors

In this example, we describe vectors in which most of the wild-type piggyBac sequences within the terminal domains have been removed from the transposon (delivery cassette) without a significant decrease in transposition efficiency.

This was achieved by including a second piggyBac sequence (modified, to make it undeliverable) in the same plasmid. This design decreased the size of the required terminal domains within the delivered gene cassette of piggyBac vectors from about 1,500 base pairs (Li et al., Insect Mol. Biol. 14:17-30 (2005)) to just 98 base pairs, the shortest sequence that allows stable transgene integration for any viral or non-viral gene delivery system that has been described to date. By removing these sequences from the delivered gene cassette, they are no longer incorporated into the host genome. This reduction in the length of DNA sequences incorporated into the target cell genome not only decreases the risk of insertional mutagenesis (Meir et al., BMC Biotechnol. 11:28 (2011)), but also eliminates any potential promoter or enhancer activity that the terminal domains might exert on host cell oncogenes (Cadinanos et al., Nucleic Acids Res, 35:e87 (2007)).

Specifically, we removed the internal domains from the gene delivery cassette leaving only the minimal terminal repeats behind and demonstrated that we could stably deliver genes to a number of different cell types with almost similar efficacy as piggyBac vectors with longer terminal domains. Only the minimal terminal repeats and the transgene were integrated into the host genome, while both the piggyBac transposase and the full-length terminal domains in the helper region of the plasmid were subsequently degraded with the plasmid. The integrated unit included only the 35 base pairs 5'-end and the 63 base pairs 3'-end, plus the transgene. This is significantly smaller than the residual (non-essential) DNA sequences left by viral or classical transposon vectors. In addition, neither the 5' nor the 3' piggyBac minTRs contain known active promoters or enhancers (Shi et al., BMC Biotechnol. 7:5 (2007); Handler et al., Proc. Natl. Acad. Sci. U.S.A. 95:7520-7525 (1998)) further improving the safety profile of these gene delivery vectors. Unlike viral vectors, transgene expression can be terminated by a strong polyadenylation signal inside the transposon providing additional protection against unwanted activation of host cell oncogenes.

Figure 4:
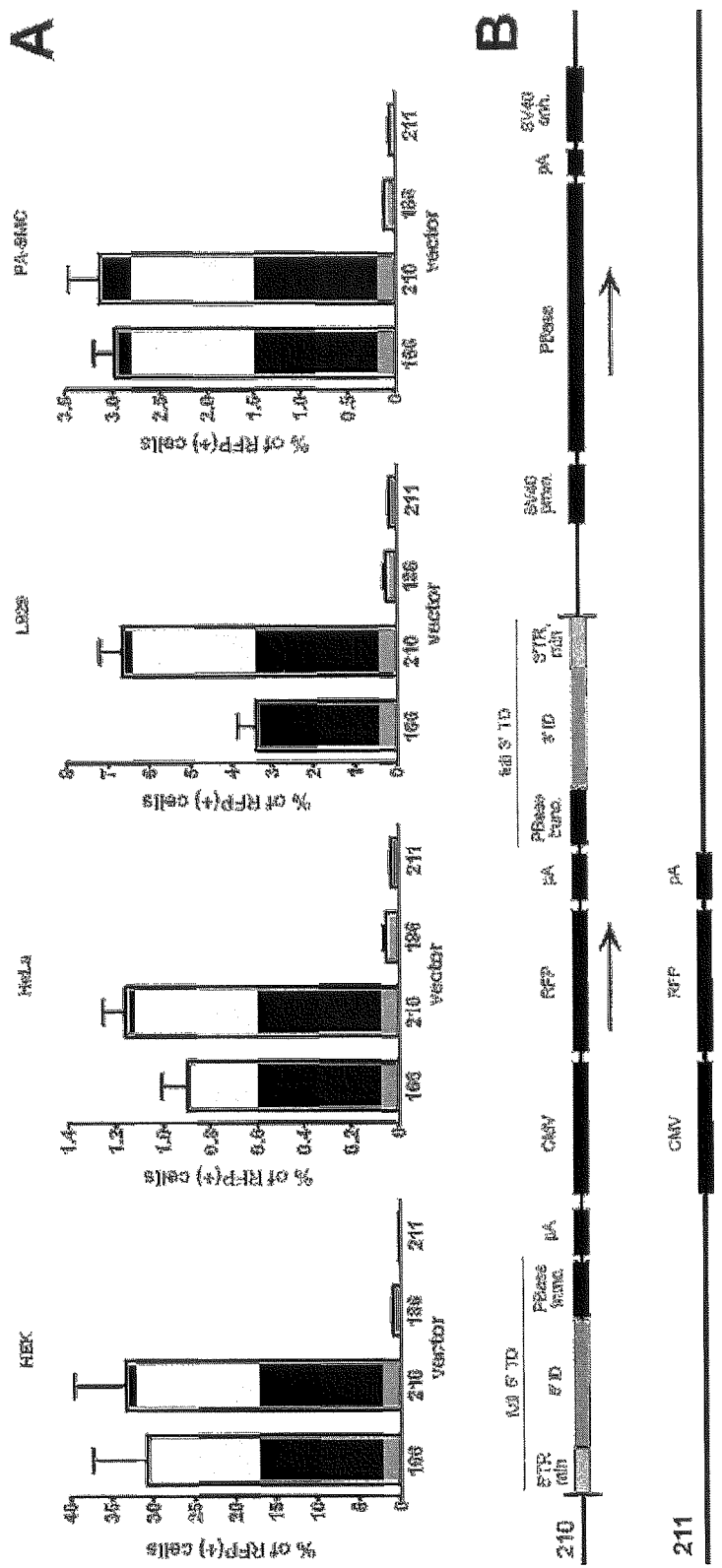
FIG. 4 (A) shows the percentage of RFP-positive target cells 28 days after transfection with the indicated transposon vectors (and indicated cell types) (n=4); and (B) shows a detailed presentation of plasmids 210 and 211. 5'TRmin, 3'TRmin: minimal 5' or 3' terminal repeats (in light gray); CMV: cytomegalovirus promoter; RFP: red fluorescent protein; pA: polyadenylation signal (SV40 polyadenylation signal to terminate RFP expression in plasmid-210 and plasmid-211, and two structurally different (synthetic) polyadenylation signals to terminate truncated and full size transposase expression in plasmid-210); 5'ID, 3'ID: internal 5' or 3' repeats that do not overlap with the transposase gene (in gray); SV40prom and SV40enh: SV40 promoter or enhancer; PBase: piggyBac transposase gene; full 5' TD, full 3' TD: 5' or 3' full length terminal domains; PBase trunc: truncated 5' piggyBac transposase gene with added stop codon in vector 210 (produces truncated transposase) and 3' truncated variant (no product). Black vertical lines indicate non-mutated TTAA integration sites flanking transposition-competent sequences. Arrows indicate the orientation of the operons. Prokaryotic origin of replication and ampicillin resistance gene are not shown. (Vectors are aligned for easier comparison, but distances between delivered cassette and helper part of plasmid are not drawn to scale).

We designed several plasmids (FIG. 1) and determined their transposition efficiency in target cells. The first plasmid contained a delivered cassette encoding the reporter gene, red fluorescent protein (RFP), flanked by 5' and 3' minTRs (plasmid-132). In a second plasmid we inserted a wild type piggyBac transposon separated from the RFP delivery cassette by 683 and 2466 base pair linkers (plasmid-137, FIGS. 1, 2B). This construct allowed us to add full-length terminal domains back into the plasmid without including them within the RFP-delivered cassette. The presence of piggy-Bac transposase in the wild type transposon (driven by its native promoter) eliminated the necessity of using a helper vector to deliver the transposase. A third plasmid (plasmid-185), also contained the RFP-delivery cassette, but included an additional (modified) full-length transposon in which both TTAA integration sites were mutated (to GTAA) to prevent transposition of the full-length piggyBac into the host genome. In plasmid-185, the full-length terminal domains of the second transposon were separated from the minTRs of the RFP delivery cassette by two linkers of 254 and 3354 base pairs. Since the activity of the native transposase promoter is unpredictable in many mammalian cells (Cadinanos et al., Nucleic Acids Res. 35:e87 (2007)), we replaced the native promoter with an SV40 promoter in this, and in subsequent plasmids (promoters are not shown in FIG. 1, refer to FIGS. 2-4 for plasmid details) to more reliably drive expression of the transposase. This replacement necessitated a partial duplication of the 5' terminal domain to keep it intact, since both the 5' and the 3' terminal domains overlap with the transposase gene8 (plasmid-185, FIG. 2B). Although these modifications made plasmid-185 more complicated than plasmid-137, the replacement of the native promoter with the SV40 promoter ensured predictable transposase expression and the mutation of the TTAA sites prevented the unwanted excision of the second transposon from the plasmid. Plasmid-186 (not shown in FIG. 1) was an inactive variant of plasmid-185 that lacked a promoter for transposase expression and was used to determine the level of non-specific integration into the host cell.

We transfected Human Embryonic Kidney (HEK)-293 cells separately with each plasmid. Two days after transfection, cells were collected and RFP-positive cells isolated using flow cytometry. These cells were then monitored for RFP expression over 28 days. Initial transfection efficiency was about 90% for all plasmids. Four weeks after transfection, only 0.07% of cells initially transfected with plasmid-132 were RFP positive (FIG. 2A). Co-transfection of plasmid-132 with a helper plasmid containing the piggyBac transposase (plasmid-200) failed to substantially increase transposition efficiency (0.13%). Transfection with plasmid-137, however, resulted in a marked increase in the number of cells stably expressing RFP at 28 days to 3.89%. These results suggested that the minTRs alone are not sufficient to allow plasmid-to-chromatin transposition, but if full-length internal domains were present elsewhere in the plasmid, even if they are located outside of the delivery cassette, successful transposition into the host cell genome could be achieved.

These results with plasmid-137 did not clarify whether only the RFP-delivery cassette was integrated into the host cell genome or whether the entire fragment, containing both piggyBac transposons, was delivered. Therefore, we tested the integration efficiency of plasmid-185, a plasmid in which the TTAA integration sites flanking the full-length piggyBac vector in the helper part of the plasmid were mutated (to GTAA), preventing its excision from the plasmid and thus preventing its integration into the host (other modifications are described in FIG. 2B). Plasmid-185 had significantly greater transposition efficiency than plasmid-137 (13.4% versus 3.89% of initially transfected cells at 28 days) (FIG. 2A). The transposition efficiency of plasmid-186 (FIG. 2), in which the transposase promoter was deleted, was reduced to background levels (0.09%) indicating that both transposase expression and full-length terminal domains are required for successful transposition.

2. Partial Truncation of the Helper Part of piggyBac Plasmid Yields Improved Transposition Efficiency Although vector-185 showed relatively high integration efficiency, it was a relatively large and complicated plasmid. Keeping the RFP delivery cassette transposon with minTRs unchanged, we tried to truncate and simplify the helper region of the plasmid to make the entire vector more compact. First, we removed the complete 5' minTR and half of the 3' minTR (including both TTAA sites) from the helper transposon to disrupt the native 5' terminal domain promoter and prevent interaction of transposase with these terminal sequences of the helper part of the vector (plasmid-166). The SV40 promoter was then moved directly in front of the entire helper region of the plasmid to drive the transposase expression since the native promoter was disrupted and rendered non-functional (FIG. 3A, plasmid-166). Since the combined effect of two sequential promoters (in the previous plasmid-185) may have led to interference, this modification not only eliminated the need for internal polyadenylation signal sequence, but also the requirement to duplicate the sequences in the 5' terminal domain that overlap with the piggyBac transposase.

This streamlined vector-166 demonstrated greater integration efficiency than vector-137 and vector-185. Thirty-two (32) percent of the initially transfected HEK cells stably incorporated and expressed the delivered transgene (RFP) at 4 weeks (FIG. 3A). Removing more sequences from the terminal domains of plasmid-166 (leaving a functional transposase gene, but markedly truncated terminal domains in the helper region) significantly reduced the plasmid's transposition efficiency (0.72%) (plasmid-206). The differences in transposition efficiency between plasmids 166 and 206 demonstrated that the presence of long internal domains flanking the transposase gene were required for the successful transposition of the piggyBac vector; these long internal domains could be located outside of the integrated transposon as long as minTRs were present within the delivered sequence.

3. Minimal Transposon Vector Allows Stable Gene Delivery in Multiple Cell Types

After testing multiple transposon plasmids in HEK-293 cells, we concluded that plasmid-166 had the highest transposition efficiency. We then tested this plasmid against one in which the RFP-delivery cassette consisted of full-length terminal domains, typical of existing piggyBac vectors. Therefore we made a piggyBac plasmid in which the RFP-delivery cassette contained the full-length terminal domains (plasmid-210, FIGS. 1, 4B) instead of the minTRs found in plasmid-166. Similar to the design of plasmid-166, plasmid-210 also contained the transposase within the same construct under the control of the SV40 promoter. These plasmids were then tested in the following cells: HEK-293, HeLa, L929 (mouse fibroblasts), and primary rat pulmonary artery smooth muscle cells (PASMC). We compared the integration efficiency of both these plasmids to that obtained with the non-transposon plasmid-211 (plasmid-211, transposon-independent integration control) and with the transposon vector-186 that had the same piggyBac sequences, but did not express transposase due to the absence of the upstream promoter.

As shown in FIG. 4B, plasmid-166 and plasmid-210 were successfully transposed in all cell types studied. HEK-293 cells were the most transposable, whereas HeLa cells were the most resistant to transposition. Although plasmid-210 demonstrated higher transposition efficiency in all cell types, the differences between the two were not marked. Both plasmid-166 and plasmid-210 had significantly higher integration efficiencies than the non-transposon naked DNA control (plasmid-211) and transposase deficient vector-186.

4. Stably Transgene-Positive Target Cells Contain Only the Delivered Transposase Sequence The preceding results demonstrated that the long internal domains could be removed from the delivered cassette to other parts of the plasmid without significantly impairing transposition efficiency. To prove that only the transposon, but not the entire plasmid, was integrated into the host genome of cells stably expressing RFP, we performed PCR on total cell DNA using distinct primers, one that amplified only the RFP-delivery cassette and another that overlapped with part of the non-delivered plasmid. Because the first 13 base pairs of both terminal repeats and the following TTAA integration sites plus the next 7 base pairs flanking the RFP delivery cassette in plasmid-166 (total 24 base pairs) are symmetrical, we used only one primer for each PCR reaction. The inner primer (TTAACCCTAGAAAGATA) (SEQ ID NO:21) was complementary to the common sequence located at both minTRs (single underline) and also included a TTAA integration site (double underline) to which they are flanked in the plasmid or in chromatin. The outer primer (GTCGACTTTAACCCTAGAA) (SEQ ID NO:22) straddled the sequences that transitioned between the non-delivered plasmid and the delivered transposon. This outer primer partially overlapped with the inner primer (single and double underlines). The part of the outer plasmid that coupled with the sequences within the transposon was 5 base pairs shorter when compared to the inner primer, yet covered an additional 7 base pairs fragment (dotted underline) located outside of the transposon and TTAA integration site in the plasmid. The outside 7 base pairs fragment at both sides is not transpositioned and therefore exists only in the plasmid. Therefore, if only the transposon is incorporated into the host cell genome, amplification of total cellular DNA with the outer primer will not generate a PCR product whereas amplification with the inner primer will. In contrast, if the entire plasmid had been incorporated into the host cell genome, both the outer and the inner primer will generate a PCR product. If only a part of the RFP delivery cassette had been incorporated, no PCR products would be generated with either primer.

We first demonstrated that PCR amplification of plasmid-166 with either the outer or the inner primer generated a PCR product with a similar size (FIG. 5A) and an identical rate of accumulation as confirmed by qPCR (data not shown). The complete sequence of the RFP delivery cassette in both PCR products was confirmed by sequence analysis. We then isolated DNA from: RFP-negative HEK-293 cells, cells stably expressing RFP 28 days after transfection with plasmid-166 (integrated), and HEK-293 cells that were initially RFP positive, but became RFP negative 28 days after being transfected with plasmid-166 (transiently transfected, nonintegrated). In addition, DNA from three different clones of HEK-293 cells that stably expressed RFP 65 days after initial transfection with plasmid-166, was analyzed.

Figure 5:
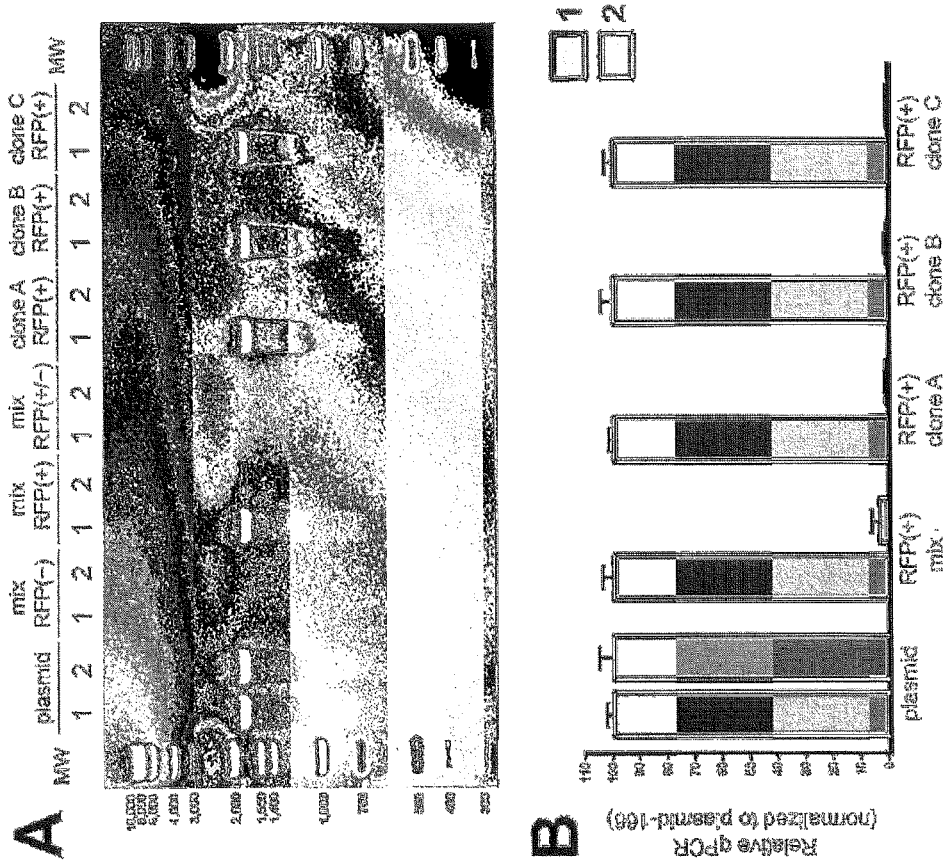
FIG. 5 (A) shows PCR of an inventive vector (plasmid-166) and genomic DNA using inner (1) and outer (2) primers, wherein plasmid: plasmid-166 DNA; RFP(−): total DNA from non-transfected HEK-293 cells (negative control); RFP(+): total DNA from cells stably expressing RFP (red fluorescent protein) 28 day post transfection (mix population or clones); RFP(+/−): total DNA from cells initially RFP positive after transfection, but RFP-negative at 28 days; clone A, B, C: RFP positive clones derived from the mixed population of RFP-positive cells (all 65 days post-transfection); and MW: molecular weight markers.

As shown in FIG. 5A, PCR amplification of DNA from cells stably expressing RFP (RFP(+)) yielded a PCR product equal to the length of the entire transposon (1,656 bp) only when the inner primer was used. Sequence analysis of this PCR fragment confirmed the presence of the intact transposon with the RFP operon. Three different RFP-positive clones isolated from a mixed population of RFP-positive HEK-293 cells each showed the same PCR product demonstrating the presence of the entire transposon. In contrast, amplification of DNA from these cells using the outer primer failed to produce a PCR product indicating that the plasmid flanking sequences were absent. Negative cells, both those that had never been transfected (RFP(−)) and those that had been transiently transfected, but were now negative after 28 days (RFP(+/−)), demonstrated no PCR product when amplified with either the inner or the outer primer (FIG. 5A). Using qPCR we demonstrated a 31-fold decrease in the signal intensity with the outer primer between the DNA from a mixed population of RFP-positive cells 28 day after transfection as compared to the inner primer and normalized to the DNA from the plasmid-166 (FIG. 5B). The small, but measurable, product accumulation seen in the mixed population of RFP-positive cells (also visible in FIG. 5A) when amplified by the outer primer was likely due to either the prolonged stability of the (nonintegrated) vector plasmid in transiently transfected cells or to non-specific integration of the plasmid into the host genome of a few cells. The three clones that remained RFP positive after 65 days showed no PCR product with the outer primer. Overall, these results demonstrate that only the transposon, and not the rest of the plasmid, was stably incorporated into the genome of the target cell. These results also demonstrate that the loss of fluorescence in the transiently transfected cells (RFP(+/−)) was due to the failure of the transposon to integrate into the host genome, rather than to inactivation of the CMV promoter controlling RFP expression.

Example 2

Schematic maps of the vectors used in this example are illustrated in FIG. 6A. In plasmid-185, the full-length terminal domains of the second transposon were separated from the minTRs of the RFP delivery cassette by two linkers of 254 bp and 3354 bp. While the second (full size) transposon demonstrated a helper effect on the integration of the RFP delivery cassette in this configuration, we hypothesized that shortening these distances would make the helper part more accessible for the transposase and further increase transposition efficiency of the vector. To test this supposition, we constructed two additional plasmids. Plasmid-196 had the same transposon components as plasmid-185, but the long terminal sequences of the helper part were rearranged. They were relocated and positioned in closer proximity to the transposable part of the vector. In this new plasmid, the distances between the minTRs and the long terminal domains were reduced to only 17 base pairs (compared to 254 bp and 3354 bp for plasmid-185) with no additional polyadenylation sequences to terminate transposase expression. Plasmid-196 had normal (TTAA) integration sites flanking the minTRs in the RFP delivery cassette and mutated (GTAA) sequences around the long terminal domains of the helper part, to prevent its excision. As a result of these changes, the second transposon was divided into two separate fragments. A second plasmid (plasmid-146) was constructed similar to plasmid-196, but the SV40 promoter and most of the transposase gene (excluding entire 3' terminal domain) were deleted. Plasmid-146 was either delivered alone or was co-transfected with a separate helper plasmid, plasmid-200, expressing transposase.

Both plasmid-196 and -146 were tested in HEK-293 cells. Cells were transfected with the corresponding transposon vector and two days later were sorted and RFP-positive cells re-seeded. Cells were monitored for RFP expression for up to 28 days post-transfection. Plasmid-185 was used as a positive control, while plasmid-186, a construct in which the transposon sequences were rearranged making it unable to express transposase, was used as a negative control. As illustrated in FIG. 6B, both plasmid-196 and -146 plasmids also yielded cells stably expressing RFP, but rather than increasing transposition efficiency, both vectors decreased it. This suggested that decreasing the distance between the delivered and helper transposons may create an additional barrier for successful transposition.

Example 3

Schematic maps of the vectors used in this example are illustrated in FIG. 7A. In the previously tested plasmids, the delivered (CMV-RFP) and helper (SV40-transposase) operons were aligned in the same orientation as the upstream 5' terminal domain and the downstream 3' terminal domain. We investigated whether a change in operon orientation would affect transposition efficiency. We constructed and tested four additional plasmids similar to plasmid-185, -166, -196 and -146, but with the delivery cassette oriented in an opposite direction to the rest of the plasmid (196R, 146R, 166R, 185R).

We tested the transposition efficiency of these "reverse" vectors with the original "forward" oriented vectors in HEK-293 cells. Two days after transfection with corresponding plasmids, RFP-positive cells were sorted and then analyzed for RFP expression 28 days later as described previously. Plasmid-146 and -146R were also co-transfected with the helper plasmid expressing the piggyBac transposase (plasmid-200). As illustrated in FIG. 7B, although all "reverse" vectors demonstrated the ability to deliver the RFP delivery cassette to the target chromatin, the transposition efficiency of these "reverse" oriented vectors was less than that of "forward" oriented vectors in all cases.

In conclusion, the working examples demonstrate that although the internal domain sequences are required for the successful transposition of piggyBac vectors, they can be positioned outside of the transposon and still perform this function, something not previously demonstrated. This novel design reduces the amount of non-essential DNA incorporated into the host genome from about 1,500 to as few as 98 base pairs and does so without significantly decreasing the integration efficiency of the vector. This reduction in non-essential DNA may decrease the risk of host cell transformation, thus making this vector safer and more attractive for use in human research.

PUBLICATIONS

U.S. Pat. No. 6,962,810
U.S. Pat. No. 7,105,343
U.S. Pat. No. 7,129,083
U.S. Patent Application Publication 2010/0221824 A1;
U.S. Patent Application Publication 2010/0154070 A1;
U.S. Patent Application Publication 2011/0311506 A1;
U.S. Patent Application Publication 2007/0204356 A1;
U.S. Patent Application Publication 2011/0047635 A1;
U.S. Patent Application Publication 2010/0240133 A1;
Wu et al., PNAS 103(41):15008-13 (2006); and
Wilson et al., Mol. Ther. 15(1):139-45 (2007).

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A genetic delivery system, the system comprising a first polynucleotide vector comprising:

a) a transposon flanked at the 5' and the 3' end by a TTAA sequence, wherein the transposon comprises a heterologous nucleic acid to be introduced into a genome of a target cell, and wherein the transposon further comprises a piggyBac 5' inverted minimal terminal repeat sequence (5' minTR) which has the nucleotide sequence of SEQ ID NO:2, or a variant thereof that differs from SEQ ID NO:2 by a single nucleotide, and a piggyBac 3' inverted terminal repeat sequence (3' minTR) which has the nucleotide sequence of SEQ ID NO:7, or a variant thereof that differs from SEQ ID NO:7 by a single nucleotide, wherein the 5' minTR and the 3' minTR flank the nucleic acid; and b) a helper portion which comprises a 5' piggyBac internal domain sequence (5' ID) which has the nucleotide sequence of SEQ ID NO:3, or a variant thereof that differs from SEQ ID NO:3 by truncation of up to 50% of the 5' nucleotides thereof that do not overlap with SEQ ID NO:4 or by truncation of up to 50% of the 3' nucleotides thereof, and a 3' piggyBac internal domain sequence (3' ID) which has the nucleotide sequence of SEQ ID NO:5, or a variant thereof which differs from SEQ ID NO:5 by truncation of up to 50% of the 5' nucleotides thereof, or by truncation of up to 50% of the 3' nucleotides thereof that do not overlap with SEQ ID NO:4; and wherein the delivery system further comprises a piggyBac transposase or a nucleic acid encoding the piggyBac transposase, wherein the nucleic acid is operably linked to a promoter that is functional in the target cell, wherein the piggyBac transposase catalyzes excision of the heterologous nucleic acid from the first polynucleotide vector and insertion of the heterologous nucleic acid into the genome of a target cell; and wherein the transposon does not contain any of the piggyBac 5' ID sequence or the piggyBac 3' ID sequence.

2. The genetic delivery system of claim 1, wherein the vector is a viral vector.

3. The genetic delivery system of claim 1, wherein the vector is a non-viral vector.

4. The genetic delivery system of claim 1, wherein the vector is a plasmid.

5. The genetic delivery system of claim 1, wherein the piggyBac 5' minTR has the nucleotide sequence of SEQ ID NO:2.

6. The genetic delivery system of claim 1, wherein the piggyBac 3' minTR has the nucleotide sequence of SEQ ID NO:7.

7. The genetic delivery system of claim 1, wherein the piggyBac 5' ID has the nucleotide sequence of SEQ ID NO:3.

8. The genetic delivery system of claim 1, wherein the piggyBac 3' ID has the nucleotide sequence of SEQ ID NO:5.

9. The genetic delivery system of claim 1, wherein the nucleic acid encoding the piggyBac transposase is located in the helper portion of the first vector.

10. The genetic delivery system of claim 9, wherein the nucleic acid encoding the piggyBac transposase is located between the piggyBac 5' ID sequence and the 3' ID sequence.

11. The genetic delivery system of claim 10, wherein the helper portion comprises the nucleotide sequence of SEQ ID NO:6.

12. The genetic delivery system of claim 10, wherein the promoter is located 5' to the helper portion.

13. The genetic delivery system of claim 12, wherein the helper portion has the nucleotide sequence of SEQ ID NO:10.

14. The genetic delivery system of claim 9, wherein the helper portion comprises a 5' portion which has the nucleotide sequence of SEQ ID NO:8, a 3' portion which has the nucleotide sequence of SEQ ID NO:9, and wherein the promoter is located between the 5' and 3' portions.

15. The genetic delivery system of claim 1, wherein the nucleic acid encoding the piggyBac transposase is not located between the piggyBac 5' ID and the piggyBac 3' ID.

16. The genetic delivery system of claim 15, wherein the helper portion comprises a 5' portion which has the nucleotide sequence of SEQ ID NO:11 and a 3' portion which has the nucleotide sequence of SEQ ID NO:12.

17. The genetic delivery system of claim 15, wherein the piggyBac 5' ID sequence and the piggyBac 3' ID sequence are separated by a linker sequence.

18. The genetic delivery system of claim 1, which comprises a second vector, wherein the second vector comprises the nucleic acid encoding the piggyBac transposase.

19. The genetic delivery system of claim 1, wherein the nucleic acid encoding the piggyBac transposase has the nucleotide sequence of SEQ ID NO:4.

20. The genetic delivery system of claim 1, wherein the vector further comprises a linker polynucleotide which is operably linked to the 3' TTAA sequence and the helper portion.

21. The genetic delivery system of claim 20, wherein the linker polynucleotide comprises from about 17 to about 3,000 nucleotides.

22. The genetic delivery system of claim 1, wherein the heterologous nucleic acid in the transposon comprises a coding sequence.

23. The genetic delivery system of claim 22, wherein the heterologous nucleic acid is operably linked to at least one regulatory sequence.

24. The genetic delivery system of claim 1, wherein the heterologous nucleic acid in the transposon comprises a non-coding sequence.

25. A method of delivering heterologous nucleic acid into the genome of a target cell, comprising introducing the genetic delivery system of claim 1 into the target cell; and culturing the target cell transformed with the genetic delivery system, wherein the transposon comprising the heterologous nucleic acid is excised from the vector and integrated into the genome of the target cell.

26. The method of claim 25, wherein the target cell is an animal cell.

27. The method of claim 26, wherein the animal cell is a stem cell.

28. The method of claim 27, wherein the stem cells are pluripotent stem cells.

\* \* \* \* \*